(12) United States Patent
Zhang et al.

(10) Patent No.: US 11,168,146 B2
(45) Date of Patent: Nov. 9, 2021

(54) COMPOSITIONS AND METHODS FOR INCREASING PROTEIN HALF-LIFE IN A SERUM

(71) Applicant: Nanjing Legend Biotech Co., Ltd., Jiangsu (CN)

(72) Inventors: Fang Liang Zhang, Jiangsu (CN); Jianbing Zhang, Orleans (CA); Shu Wu, Jiangsu (CN)

(73) Assignee: Nanjing Legend Biotech Co., Ltd., Jiangsu (CN)

(*) Notice: Subject to any disclaimer, the term of this patent is extended or adjusted under 35 U.S.C. 154(b) by 339 days.

(21) Appl. No.: 16/458,872

(22) Filed: Jul. 1, 2019

(65) Prior Publication Data

US 2019/0330370 A1  Oct. 31, 2019

Related U.S. Application Data

(62) Division of application No. 14/903,156, filed as application No. PCT/US2014/047768 on Jul. 8, 2014, now Pat. No. 10,407,508.

(60) Provisional application No. 61/843,628, filed on Jul. 8, 2013.

(51) Int. Cl.
*C07K 16/34* (2006.01)
*C07K 16/18* (2006.01)

(52) U.S. Cl.
CPC .............. *C07K 16/34* (2013.01); *C07K 16/18* (2013.01); *C07K 2317/22* (2013.01); *C07K 2317/565* (2013.01); *C07K 2317/569* (2013.01); *C07K 2317/94* (2013.01); *C07K 2319/00* (2013.01); *C07K 2319/30* (2013.01)

(58) Field of Classification Search
None
See application file for complete search history.

(56) References Cited

U.S. PATENT DOCUMENTS

| | | |
|---|---|---|
| 6,555,114 B1 | 4/2003 | Leroux-Roels et al. |
| 7,250,166 B2 | 7/2007 | Drakenberg et al. |
| 8,101,393 B2 | 1/2012 | Gray et al. |
| 8,147,836 B2 | 4/2012 | Wood et al. |
| 8,349,326 B2 | 1/2013 | Shoemaker et al. |
| 2003/0226155 A1 | 12/2003 | Sadeghi et al. |
| 2007/0031440 A1* | 2/2007 | Prior ............... C07K 16/241 424/178.1 |
| 2010/0291023 A1* | 11/2010 | Schuurman .......... C07K 16/283 424/85.2 |
| 2010/0310464 A1 | 12/2010 | Cicortas Gunnarsson et al. |
| 2011/0021757 A1 | 1/2011 | Tamura et al. |
| 2011/0262427 A1 | 10/2011 | Hermans et al. |

FOREIGN PATENT DOCUMENTS

| | | | |
|---|---|---|---|
| JP | 2006-520584 A | 9/2006 | |
| JP | 2010539921 A | 12/2010 | |
| JP | 2013520974 A | 6/2013 | |
| WO | 2004041865 A2 | 5/2004 | |
| WO | WO-2004041862 A2 * | 5/2004 | ........... C07K 16/249 |
| WO | 2005/118642 A2 | 12/2005 | |
| WO | 2007/120864 A2 | 10/2007 | |
| WO | 2009040562 A1 | 4/2009 | |
| WO | 2009/059972 A2 | 5/2009 | |
| WO | 2011107507 A1 | 9/2011 | |
| WO | 2013071127 A1 | 5/2013 | |
| WO | 2013/142167 A1 | 9/2013 | |

OTHER PUBLICATIONS

Orlandini et al., Protein Sci. Sep. 1994;3(9):1476-84. doi: 10.1002/pro.5560030913.*
International Search Report and Written Opinion dated Feb. 10, 2015 in PCT/US2014/45768.
Sleep et al., "Albumin as a Versatile Platform for Drug Half-Life Extension", Biochim Biophys Acta., vol. 1830, pp. 5526-5534 (2013).
Kontermann, "Strategies for Extended Serum Half-Life of Protein Therapeutics", Curr Opin Biotechnol., vol. 22, No. 3, pp. 868-876 (2011).
Lee et al., "Prolonged Circulating Lives of Single-Chain Fv Proteins Conjugated with Polyethylene Glycol: A Comparison of Conjugation Chemistries and Compounds", Bioconjug Chem., vol. 10, No. 6, pp. 973-981 (1999).
Tuettenberg et al., "Pharmacokinetics, Pharmacodynamics, Safety and Tolerability of APG101, a CD95-Fc Fusion Protein, in Healthy Volunteers and Two Glioma Patients", Int. Immunopharmacol. vol. 13, No. 1, pp. 93-100 (2012).
Nolte et al., "Improved Kinetics of rIX-FP, a Recombinant Fusion Protein Linking Factor IX with Abumin, in Cynomolgus Monkeys and Hemophilia B Dogs", J. Thromb Haemost., vol. 10, No. 8, pp. 1591-1599 (2012).
Walker et al., "Anti-serum Albumin Domain Antibodies in the Development of Highly Potent, Efficacious and Long-Acting Interferon", Protein Eng. Des. Sel., vol. 23, No. 4, pp. 271-278 (2010).
Stork et al., "A Novel Tri-Functional Antibody Fusion Protein with Improved Pharmacokinetic Properties Generated by Fusing a Bispecific Single-Chain Diabody with an Albumin-Binding Domain from Streptococcal", Protein G. Protein Eng. Des. Sel., vol. 20, No. 11, pp. 569-576 (2007).
Matsubara et al., "Single Dose GLP-1-Tf Ameliorates Myocardial Ischemia/reperfusin Injury", J. Surg Res., vol. 165, No. 1, pp. 38-45 (2011).
Keefe et al., "In Vitro Characterization of an Acetylcholine Receptor-Transferrin Fusion Protein for the Treatment of Myasthenia Gravis", Autoimmunity, vol. 43, No. 8, pp. 628-639 (2010).

(Continued)

*Primary Examiner* — Michael Szperka
(74) *Attorney, Agent, or Firm* — Ice Miller LLP

(57) ABSTRACT

Novel antibodies, such as single domain antibodies (sdAbs), or fragments thereof that specifically bind a transferrin are described. Compositions, methods and systems for increasing the half-life of a target protein in a serum using an antibody or fragment thereof against a transferrin are described.

20 Claims, 8 Drawing Sheets

Specification includes a Sequence Listing.

(56) References Cited

OTHER PUBLICATIONS

Arbabi et al., "Selection and Identification of Single Domain Antibody Fragments from Camel Heavy-Chain Antibodies", FEBS Lett, vol. 414, No. 3, pp. 521-526 (1997).
Tanha et al., "Phage Display Technology for Identifying Specific Antigens on Brain Endothelial Cells", Methods Mol Med., vol. 89, pp. 435-449 (2003).
Zhang et al., "A Pentavalent Single-Domain Antibody Approach to Tumor Antigen Discovery and the Development of Novel Proteomics Reagents", J. Mol. Biol., vol. 341, No. 1, pp. 161-169 (2003).
Cortez-Retamozo et al., "Efficient Cancer Therapy with a Nanobody-Based Conjugate", Cancer Res., vol. 64, No. 3, pp. 2853-2857 (2004).
Luo et al., Correlation of Pharmacokinetics with the Antitumor Activity of Cetuximab in Nude Mice Bearing the GEO Human Colon Carcinoma Xenograft, Cancer Chemother Pharmacol., vol. 56, No. 5, pp. 455-464 (2005).
Ali et al., Transferrin Trojan Horses as a Rational Approach for the Biological Delivery of Therapeutic Peptide Domains, Journal of Biological Chemistry, vol. 274, No. 34, p. 24066-24073 (1999).
Int'l Report on Patentability dated Jan. 21, 2016 in Int'l Application No. PCT/US2014/045768.
Office Action dated Jan. 10, 2017 in JP Application No. 2016-525430.
Orlandini et al., "Cloning, Characterization, and Modeling of a Monoclonal Anti-human Transferrin Antibody that Competes with the Transferrin Receptor", Protein Science, vol. 3, pp. 1476-1484 (1994).
Partial Supplementary European Search Report dated Feb. 28, 2017 in EP Application No. 14822180.
Chang et al., "Advances and Challenges in Developing Cyokine Fusion Proteins as Improved Therapeutics", Expert Opinioins, vol. 4, No. 2, pp. 181-194 (2009).
Dennis et al., "Transferrin Antibodies into the Brain", Neuro Reviews, vol. 37, pp. 301-302 (2012).
Holt et al.,. Anti-Serum Albumin Domain Antibodies for Extending the Half-Lives of Short Lived Drugs, Protein Engineering Design & Selection, vol. 21, No. 5, pp. 283-288 (Apr. 2008).
Muyldermans et al., "Camelid Immunoglobulins and Nanobody Technology", Vet. Immun. and Immun., vol. 128, pp. 178-183 (2009).
Extended European Search Report dated Jun. 7, 2017 in EP Application No. 14822180.7.
Office Action dated Nov. 7, 2017 in JP Application No. 2016525430.
Office Action dated Oct. 1, 2018 in EP Application No. 14822180.7.
Hoefman et al., "Pre-Clinical Intravenous Serum Pharmacokinetics of Albumin Binding and Non-Half-Life Extended Nanobodies," Antibodies, vol. 4, pp. 141-156 (2015).
Harmsen et al., "Properties, production, and applications of camelid single-domain antibody fragments," Appl. Microbiol Biotechnol., vol. 77, pp. 13-22 (2007).
Janeway, et al., "Immunobiology: The Immune System in Health and Disease", Third Edition, 19097, Garland Press, p. 3:1-3:11,(1997).
Rudikoff, et al., "Single amino acide substitution altering antigen-binding specificity", Proc. Natl. Acad. Sci., vol. 79, pp. 1979-1983 (Mar. 1982).
Ghahroudi, et al., "Selection and identification of single domain antibody fragments from camel heavy-chain antibodies", FEBS Letters, 414, pp. 521-526, (1997).
Casey, et al., "Protein Engineering, Design, and Selection", vol. 13, Issue 6, pp. 445-452.

* cited by examiner

FIG. 2

| | <FR1-Kabat> | <CDR1-Kabat> | <FR2-Kabat> | <CDR2-Kabat> | <FR3-Kabat> | <CDR3-Kabat> | <FR4-Kabat> |
|---|---|---|---|---|---|---|---|
| A60219 | QVQLVESGGGLVQAGGSLRLSCVAS | GSGFGINGVI | WYRQAFGKQRELVA | LIKSDG-YTNYRESVKG | RFTISRD-DAKNTVWLQMNALEPEDTGVYYCKT | PGVP---------- | FGQGTQVTVSS |
| A13152 | QVQLVESGGGLVQAGGSLRLSCVAP | GSGFGINGVI | WYRQAPGKQRELVA | LIKSDG-YTNYRESVKG | RFTISRD-DAKNTVWLQMNALEPEDTGVYYCKT | PGVP---------- | FGQGTQVTVSS |
| A12722 | QVKLEESGGGLVQAGGSLRLSCVAS | GSGFGINGVI | WYRQAPGKQRELVA | LIKSDG-YTNYRESVKG | RFTISRD-DAKNTVWLQMNALEPEDTGVYYCKT | PGVP---------- | FGQGTPVTVSS |
| A12630 | QVKLEESGGGLVQAGGSLRLSCVAS | GSGFGINGVI | WYRQAPGKQRELVA | LIKSDG-YTNYRESVKG | RFTISRD-DAKNTVWLQMNALEPEDTGVYYCKT | PGVP---------- | FGQGTQVTVSS |
| A12690 | QVQLVESGGGLVQPGGSLRLSCVAS | GSGFGINGVI | WYRQAPGKRRELVA | LIKSDG-YTNYRESVKG | RFTISRD-DAKNTVWLQMNALEPEDTGVYYCKT | PGVP---------- | FGQGTQVTVSS |
| A13154 | QVQLVESGGGLVQAGGSLRLSCVAS | GSGFGINGVI | WYRQAPGKQRELVA | LIKSDG-YTNYRESVKG | RFTISRD-DAKNTVWLQMNALEPEDTGVYYCKT | PGVP---------- | FGQGTQVTVSS |
| A13146 | AVQLVDSGGGLVQAGGSLRLSCVAS | GSGFGINGVI | WYRQAPGKQRELVA | LIKSDG-YTNYRESVKG | RFTISRD-DAKNTVWLQMNALEPEDTGVYYCKT | PGVP---------- | FGQGTQVTVSS |
| A13149 | QVQLVDSGGGLVQPGGSLRLSCVAS | GSGFGINGVI | WYRQAFGKQRELVA | LIKSDG-YTNYRESVKG | RFTISRD-DAKNTVWLQMNALEPEDTGVYYCKT | PGVP---------- | FGQGTQVTVSS |
| A12666 | QVKLEESGGGLVQAGGSLRLSCVAS | GSGFGVNGVI | WYRQAPGKQRELVA | LIKSDG-YTNYRESVKG | RFTISRD-DAKNTVWLQMNALEPEDTGVYYCKT | PGVP---------- | FGQGTQVTVSS |
| A12659 | EVQLVECGGGLVQAGGSLRLSCVAS | GSGFGINGVI | WYRQAPGKQRELVA | LIKSDG-YTNYRESVKG | RFTISRD-DARNTVWLQMNALEPEDTGVYYCKT | PGVP---------- | FGQGTQVTVSS |
| A13355 | QVKLEESGGGLVQAGGSLRLSCVAS | GSGFGINGVI | WYRQAPGKQRELVA | LIKSDG-YTNYRESVRG | RFTISRD-DAKNTVWLQMNALEPEDTGVYYCKT | PGVP---------- | FGQGTQVTVSS |
| A12692 | EVQLVECGGGLVQAGGSLRLSCVAS | GSGFGINGVI | WYRQAPGKQRELVA | LIKSDG-YTNYRESVKG | RFTISRD-DAKNTVWLQMNALEPEDTGVYYCKT | PGVP---------- | FGQGTQVTVSS |
| A60401 | QVKLEESGGGLVQAGGSLRLSCEAS | GNVFTIAAMG | WFRQAPGKERELVA | GITTGG-STNYADSVKG | RFTISRD-NAQNTMYLQMNSLRPEDTAAYSCNA | VTKWAARVGGSAEYEY | WGQGTQVTVSS |
| A13376 | QVKLEESGGGLVQAGGSLRLSCAAS | GNVFTIAAMA | WYRQAPGKEREVVS | GITTGG-STNYADSVKG | RFTISRD-NAQNTMYLQMNSLRPEDTAVYFCNA | VTKWAARVGGSAEYEY | WGQGTQVTVSS |
| A69476 | QVKLEESGGGLVQPGGSLRLSCAAS | GNVFTIDAMG | WYRQAPGKEREVVV | GMTNGG-KTNYADSVKG | RFTISRD-NAKNTVSLQMNSLKPEDTAVYCYA | RSKLIATINNP---YDY | WGQGTQVTVSS |
| A69449 | QVQLVESGGGVVQAGGSLRLSCVAS | GSVFSIDAMG | WYRQAPGNQRELVA | AMTNAG-STNYADSVKG | RFTISRD-NAENTVYLQMNSLKPEDTAVYYCYA | RSKLIARINNP---YEY | WGQGTQVTVSS |
| A69433 | QVKLEESGGGLVQPGGSLRLSCVAS | GNVFGIDAVG | WYRQAPGKQRELVA | ATTTSGS-STNYADSVKG | RFTISRD-IAKNTVYLQMDSLKPEDTAVYYCYA | RPKQATLIRD----DY | WGQGTQVTVSS |
| A69441 | QVKLEESGGGLVQPGGSLRLSCAAS | GSIFSIKVMG | WYRQAPGKQRELVA | DITSGG-STDYSDSVKG | RFTISRD-NAKNTVYLQMNSLKPEDTAVYYCNA | DLGCSGAGSCP---DY | WGQGTQVTVSS |
| A69447 | QVKLEESGGGSVQAGGSLRLSCTGS | GSIFPLNDMG | WYRQAPGKQRELVA | TITRGG-TTNYADSVKG | RFTISRDSNAKNTVYLQMNSLKVEDTAVYYCNM | DNRVGGS--------Y | WGQGTQVTVSS |

SEQUENCE LISTING

<160> NUMBER OF SEQ ID NOS: 70

<210> SEQ ID NO 1
<211> LENGTH: 10
<212> TYPE: PRT
<213> ORGANISM: Artificial Sequence

```
<220> FEATURE:
<223> OTHER INFORMATION: CDR1 sequence of antibody or fragment thereof
      that specifically binds transferrin

<400> SEQUENCE: 1

Gly Ser Gly Phe Gly Ile Asn Gly Val Ile
1               5                   10

<210> SEQ ID NO 2
<211> LENGTH: 10
<212> TYPE: PRT
<213> ORGANISM: Artificial Sequence
<220> FEATURE:
<223> OTHER INFORMATION: CDR1 sequence of antibody or fragment thereof
      that specifically binds transferrin

<400> SEQUENCE: 2

Gly Ser Gly Phe Gly Val Asn Gly Val Ile
1               5                   10

<210> SEQ ID NO 3
<211> LENGTH: 10
<212> TYPE: PRT
<213> ORGANISM: Artificial Sequence
<220> FEATURE:
<223> OTHER INFORMATION: CDR1 sequence of antibody or fragment thereof
      that specifically binds transferrin

<400> SEQUENCE: 3

Gly Asn Val Phe Thr Ile Ala Ala Met Gly
1               5                   10

<210> SEQ ID NO 4
<211> LENGTH: 10
<212> TYPE: PRT
<213> ORGANISM: Artificial Sequence
<220> FEATURE:
<223> OTHER INFORMATION: CDR1 sequence of antibody or fragment thereof
      that specifically binds transferrin

<400> SEQUENCE: 4

Gly Asn Val Phe Thr Ile Ala Ala Met Ala
1               5                   10

<210> SEQ ID NO 5
<211> LENGTH: 10
<212> TYPE: PRT
<213> ORGANISM: Artificial Sequence
<220> FEATURE:
<223> OTHER INFORMATION: CDR1 sequence of antibody or fragment thereof
      that specifically binds transferrin

<400> SEQUENCE: 5

Gly Asn Val Phe Thr Ile Asp Ala Met Gly
1               5                   10

<210> SEQ ID NO 6
<211> LENGTH: 10
<212> TYPE: PRT
<213> ORGANISM: Artificial Sequence
<220> FEATURE:
<223> OTHER INFORMATION: CDR1 sequence of antibody or fragment thereof
      that specifically binds transferrin

<400> SEQUENCE: 6

Gly Ser Val Phe Ser Ile Asp Ala Met Gly
1               5                   10
```

```
<210> SEQ ID NO 7
<211> LENGTH: 10
<212> TYPE: PRT
<213> ORGANISM: Artificial Sequence
<220> FEATURE:
<223> OTHER INFORMATION: CDR1 sequence of antibody or fragment thereof
      that specifically binds transferrin

<400> SEQUENCE: 7

Gly Asn Val Phe Gly Ile Asp Ala Val Gly
1               5                   10

<210> SEQ ID NO 8
<211> LENGTH: 10
<212> TYPE: PRT
<213> ORGANISM: Artificial Sequence
<220> FEATURE:
<223> OTHER INFORMATION: CDR1 sequence of antibody or fragment thereof
      that specifically binds transferrin

<400> SEQUENCE: 8

Gly Ser Ile Phe Ser Ile Lys Val Met Gly
1               5                   10

<210> SEQ ID NO 9
<211> LENGTH: 10
<212> TYPE: PRT
<213> ORGANISM: Artificial Sequence
<220> FEATURE:
<223> OTHER INFORMATION: CDR1 sequence of antibody or fragment thereof
      that specifically binds transferrin

<400> SEQUENCE: 9

Gly Ser Ile Phe Pro Leu Asn Asp Met Gly
1               5                   10

<210> SEQ ID NO 10
<211> LENGTH: 16
<212> TYPE: PRT
<213> ORGANISM: Artificial Sequence
<220> FEATURE:
<223> OTHER INFORMATION: CDR2 sequence of antibody or fragment thereof
      that specifically binds transferrin

<400> SEQUENCE: 10

Leu Ile Lys Ser Asp Gly Tyr Thr Asn Tyr Arg Glu Ser Val Lys Gly
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: CDR2 sequence of antibody or fragment thereof
      that specifically binds transferrin

<400> SEQUENCE: 11

Leu Ile Lys Ser Asp Gly Tyr Thr Asn Tyr Arg Glu Ser Val Arg Gly
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: CDR2 sequence of antibody or fragment thereof
      that specifically binds transferrin
```

```
<400> SEQUENCE: 12

Gly Ile Thr Thr Gly Gly Ser Thr Asn Tyr Ala Asp Ser Val Lys Gly
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: CDR2 sequence of antibody or fragment thereof
      that specifically binds transferrin

<400> SEQUENCE: 13

Gly Met Thr Asn Gly Gly Lys Thr Asn Tyr Ala Asp Ser Val Lys Gly
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: CDR2 sequence of antibody or fragment thereof
      that specifically binds transferrin

<400> SEQUENCE: 14

Ala Met Thr Asn Ala Gly Ser Thr Asn Tyr Ala Asp Ser Val Lys Gly
1               5                   10                  15

<210> SEQ ID NO 15
<211> LENGTH: 17
<212> TYPE: PRT
<213> ORGANISM: Artificial Sequence
<220> FEATURE:
<223> OTHER INFORMATION: CDR2 sequence of antibody or fragment thereof
      that specifically binds transferrin

<400> SEQUENCE: 15

Ala Thr Thr Thr Ser Gly Ser Ser Thr Asn Tyr Ala Asp Ser Val Lys
1               5                   10                  15

Gly

<210> SEQ ID NO 16
<211> LENGTH: 16
<212> TYPE: PRT
<213> ORGANISM: Artificial Sequence
<220> FEATURE:
<223> OTHER INFORMATION: CDR2 sequence of antibody or fragment thereof
      that specifically binds transferrin

<400> SEQUENCE: 16

Asp Ile Thr Ser Gly Gly Ser Thr Asp Tyr Ser Asp Ser Val Lys Gly
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: CDR2 sequence of antibody or fragment thereof
      that specifically binds transferrin

<400> SEQUENCE: 17

Thr Ile Thr Arg Gly Gly Thr Thr Asn Tyr Ala Asp Ser Val Lys Gly
1               5                   10                  15

<210> SEQ ID NO 18
```

```
<211> LENGTH: 4
<212> TYPE: PRT
<213> ORGANISM: Artificial Sequence
<220> FEATURE:
<223> OTHER INFORMATION: CDR3 sequence of antibody or fragment thereof
      that specifically binds transferrin

<400> SEQUENCE: 18

Pro Gly Val Pro
1

<210> SEQ ID NO 19
<211> LENGTH: 15
<212> TYPE: PRT
<213> ORGANISM: Artificial Sequence
<220> FEATURE:
<223> OTHER INFORMATION: CDR3 sequence of antibody or fragment thereof
      that specifically binds transferrin

<400> SEQUENCE: 19

Val Thr Lys Trp Ala Ala Arg Val Gly Gly Ser Ala Glu Tyr Glu
1               5                   10                  15

<210> SEQ ID NO 20
<211> LENGTH: 14
<212> TYPE: PRT
<213> ORGANISM: Artificial Sequence
<220> FEATURE:
<223> OTHER INFORMATION: CDR3 sequence of antibody or fragment thereof
      that specifically binds transferrin

<400> SEQUENCE: 20

Arg Ser Lys Leu Ile Ala Thr Ile Asn Asn Pro Tyr Asp Tyr
1               5                   10

<210> SEQ ID NO 21
<211> LENGTH: 14
<212> TYPE: PRT
<213> ORGANISM: Artificial Sequence
<220> FEATURE:
<223> OTHER INFORMATION: CDR3 sequence of antibody or fragment thereof
      that specifically binds transferrin

<400> SEQUENCE: 21

Arg Ser Lys Leu Ile Ala Arg Ile Asn Asn Pro Tyr Glu Tyr
1               5                   10

<210> SEQ ID NO 22
<211> LENGTH: 12
<212> TYPE: PRT
<213> ORGANISM: Artificial Sequence
<220> FEATURE:
<223> OTHER INFORMATION: CDR3 sequence of antibody or fragment thereof
      that specifically binds transferrin

<400> SEQUENCE: 22

Arg Pro Lys Gln Ala Thr Leu Ile Arg Asp Asp Tyr
1               5                   10

<210> SEQ ID NO 23
<211> LENGTH: 13
<212> TYPE: PRT
<213> ORGANISM: Artificial Sequence
<220> FEATURE:
<223> OTHER INFORMATION: CDR3 sequence of antibody or fragment thereof
      that specifically binds transferrin

<400> SEQUENCE: 23
```

Asp Leu Gly Cys Ser Gly Ala Gly Ser Cys Pro Asp Tyr
1               5                   10

<210> SEQ ID NO 24
<211> LENGTH: 8
<212> TYPE: PRT
<213> ORGANISM: Artificial Sequence
<220> FEATURE:
<223> OTHER INFORMATION: CDR3 sequence of antibody or fragment thereof
      that specifically binds transferrin

<400> SEQUENCE: 24

Asp Asn Arg Val Gly Gly Ser Tyr
1               5

<210> SEQ ID NO 25
<211> LENGTH: 336
<212> TYPE: DNA
<213> ORGANISM: Artificial Sequence
<220> FEATURE:
<223> OTHER INFORMATION: nucleotide sequence encoding A60219 sdAb

<400> SEQUENCE: 25
caggtacagc tggtggagtc tgggggaggc ttggtgcagg ctgggggtc tctgagactc      60 tcctgtgtag cctcgggaag cggcttcggg atcaatggcg tgatctggta tcgccaggct     120
ccagggaagc agcgcgagtt ggtcgcgctt attaagagtg acggttatac aaattataga     180
gagtccgtga agggccgatt caccatctcc agagacgacg ccaagaacac ggtgtggctg     240
caaatgaacg ccctggaacc tgaggacaca ggcgtctatt actgtaaaac acccggagta     300
ccgtttggtc agggggaccca ggtcaccgtc tcctca                              336

<210> SEQ ID NO 26
<211> LENGTH: 112
<212> TYPE: PRT
<213> ORGANISM: Artificial Sequence
<220> FEATURE:
<223> OTHER INFORMATION: A60219 sdAb sequence

<400> SEQUENCE: 26

Gln Val Gln Leu Val Glu Ser Gly Gly Gly Leu Val Gln Ala Gly Gly
1               5                   10                  15

Ser Leu Arg Leu Ser Cys Val Ala Ser Gly Ser Gly Phe Gly Ile Asn
            20                  25                  30

Gly Val Ile Trp Tyr Arg Gln Ala Pro Gly Lys Gln Arg Glu Leu Val
        35                  40                  45

Ala Leu Ile Lys Ser Asp Gly Tyr Thr Asn Tyr Arg Glu Ser Val Lys
    50                  55                  60

Gly Arg Phe Thr Ile Ser Arg Asp Asp Ala Lys Asn Thr Val Trp Leu
65                  70                  75                  80

Gln Met Asn Ala Leu Glu Pro Glu Asp Thr Gly Val Tyr Tyr Cys Lys
                85                  90                  95

Thr Pro Gly Val Pro Phe Gly Gln Gly Thr Gln Val Thr Val Ser Ser
            100                 105                 110

<210> SEQ ID NO 27
<211> LENGTH: 372
<212> TYPE: DNA
<213> ORGANISM: Artificial Sequence
<220> FEATURE:
<223> OTHER INFORMATION: nucleotide sequence encoding A60401 sdAb

<400> SEQUENCE: 27
caggtaaagc tggaggagtc tgggggaggc ttggtgcagg ctgggggtc tctgagactc 60 tcctgtgaag cctctggaaa cgtcttcact atcgctgcca tggctggtt ccgccaggct 120 ccagggaagg agcgcgagtt agtcgcaggg attactactg gtggtagcac aaactatgca 180
gactccgtga agggccgatt caccatctcc agagacaacg cacagaacac aatgtatctg 240
caaatgaaca gcctgagacc tgaggatacg ccgcctatt cctgtaatgc agtgacgaag 300
tgggcggccc gggttggggg aagtgccgag tatgagtact ggggccaggg acccaggtc 360 accgtctcct ca 372

```
<210> SEQ ID NO 28
<211> LENGTH: 124
<212> TYPE: PRT
<213> ORGANISM: Artificial Sequence
<220> FEATURE:
<223> OTHER INFORMATION: A60401 sdAb sequence

<400> SEQUENCE: 28
```

Gln Val Lys Leu Glu Glu Ser Gly Gly Gly Leu Val Gln Ala Gly Gly
1               5                   10                  15

Ser Leu Arg Leu Ser Cys Glu Ala Ser Gly Asn Val Phe Thr Ile Ala
            20                  25                  30

Ala Met Gly Trp Phe Arg Gln Ala Pro Gly Lys Glu Arg Glu Leu Val
        35                  40                  45

Ala Gly Ile Thr Thr Gly Gly Ser Thr Asn Tyr Ala Asp Ser Val Lys
    50                  55                  60

Gly Arg Phe Thr Ile Ser Arg Asp Asn Ala Gln Asn Thr Met Tyr Leu
65                  70                  75                  80

Gln Met Asn Ser Leu Arg Pro Glu Asp Thr Ala Ala Tyr Ser Cys Asn
                85                  90                  95

Ala Val Thr Lys Trp Ala Ala Arg Val Gly Gly Ser Ala Glu Tyr Glu
            100                 105                 110

Tyr Trp Gly Gln Gly Thr Gln Val Thr Val Ser Ser
        115                 120

```
<210> SEQ ID NO 29
<211> LENGTH: 336
<212> TYPE: DNA
<213> ORGANISM: Artificial Sequence
<220> FEATURE:
<223> OTHER INFORMATION: nucleotide sequence encoding A13152 sdAb

<400> SEQUENCE: 29
```
caggtacagc tggtggagtc tgggggaggc ttggtgcagg ctgggggtc tctgagactc 60 tcctgtgtag ccccgggaag cggcttcggg atcaatggcg tgatctggta tcgccaggct 120
ccagggaagc agcgcgagtt ggtcgcgctt attaagagtg acggttatac aaattataga 180
gagtccgtga agggccgatt caccatctcc agagacgacg ccaagaacac ggtgtggctg 240
caaatgaacg ccctggaacc tgaggacaca ggcgtctatt actgtaaaac acccggagta 300
ccgtttggtc aggggaccca ggtcaccgtc tcctca 336

```
<210> SEQ ID NO 30
<211> LENGTH: 112
<212> TYPE: PRT
<213> ORGANISM: Artificial Sequence
<220> FEATURE:
<223> OTHER INFORMATION: A13152 sdAb sequence
```

<400> SEQUENCE: 30

Gln Val Gln Leu Val Glu Ser Gly Gly Gly Leu Val Gln Ala Gly
1               5                   10                  15

Ser Leu Arg Leu Ser Cys Val Ala Pro Gly Ser Gly Phe Gly Ile Asn
            20                  25                  30

Gly Val Ile Trp Tyr Arg Gln Ala Pro Gly Lys Gln Arg Glu Leu Val
            35                  40                  45

Ala Leu Ile Lys Ser Asp Gly Tyr Thr Asn Tyr Arg Glu Ser Val Lys
        50                  55                  60

Gly Arg Phe Thr Ile Ser Arg Asp Asp Ala Lys Asn Thr Val Trp Leu
65                  70                  75                  80

Gln Met Asn Ala Leu Glu Pro Glu Asp Thr Gly Val Tyr Tyr Cys Lys
                85                  90                  95

Thr Pro Gly Val Pro Phe Gly Gln Gly Thr Gln Val Thr Val Ser Ser
            100                 105                 110

<210> SEQ ID NO 31
<211> LENGTH: 372
<212> TYPE: DNA
<213> ORGANISM: Artificial Sequence
<220> FEATURE:
<223> OTHER INFORMATION: nucleotide sequence encoding A13376 sdAb

<400> SEQUENCE: 31
caggtaaagc tggaggagtc tggggggaggc ttggtgcagg ctggggggtc tctgagactc      60
tcctgtgcag cctctggaaa cgtcttcact atcgctgcca tggcctggta ccgccaggct     120
ccagggaagg agcgcgagtt agtcgcaggg attactactg gtggtagcac aaattatgca     180
gactccgtga aggccgatt caccatctcc agagacaacg cacagaacac gatgtatctg     240
caaatgaaca gcctgagacc tgaggatacg gccgtctatt tctgtaatgc agtgacgaag     300
tgggcggccc gggttggggg aagtgccgag tatgagtact ggggccaggg gacccaggtc     360
accgtctcct ca                                                         372

<210> SEQ ID NO 32
<211> LENGTH: 124
<212> TYPE: PRT
<213> ORGANISM: Artificial Sequence
<220> FEATURE:
<223> OTHER INFORMATION: A13376 sdAb sequence

<400> SEQUENCE: 32

Gln Val Lys Leu Glu Glu Ser Gly Gly Gly Leu Val Gln Ala Gly Gly
1               5                   10                  15

Ser Leu Arg Leu Ser Cys Ala Ala Ser Gly Asn Val Phe Thr Ile Ala
            20                  25                  30

Ala Met Ala Trp Tyr Arg Gln Ala Pro Gly Lys Glu Arg Glu Leu Val
            35                  40                  45

Ala Gly Ile Thr Thr Gly Gly Ser Thr Asn Tyr Ala Asp Ser Val Lys
        50                  55                  60

Gly Arg Phe Thr Ile Ser Arg Asp Asn Ala Gln Asn Thr Met Tyr Leu
65                  70                  75                  80

Gln Met Asn Ser Leu Arg Pro Glu Asp Thr Ala Val Tyr Phe Cys Asn
                85                  90                  95

Ala Val Thr Lys Trp Ala Ala Arg Val Gly Gly Ser Ala Glu Tyr Glu
            100                 105                 110

Tyr Trp Gly Gln Gly Thr Gln Val Thr Val Ser Ser

<210> SEQ ID NO 33
<211> LENGTH: 336
<212> TYPE: DNA
<213> ORGANISM: Artificial Sequence
<220> FEATURE:
<223> OTHER INFORMATION: nucleotide sequence encoding A12722 sdAb

<400> SEQUENCE: 33

```
caggtaaagc tggaggagtc tgggggcgga ttggtgcagg ctggggggtc tctgagactc        60
tcctgtgtag cctcgggaag cggcttcggg atcaatggcg tgatctggta tcgccaggct       120
ccagggaagc agcgcgagtt ggtcgcgctt attaagagtg acggttatac aaattataga       180
gagtccgtga aggccgatt caccatctcc agagacgacg ccaagaacac ggtgtggctg        240
caaatgaacg ccctggaacc tgaggacaca ggcgtctatt actgtaaaac acccggagta       300
ccgtttggtc aggggacccc cgtcaccgtc tcctca                                 336
```

<210> SEQ ID NO 34
<211> LENGTH: 112
<212> TYPE: PRT
<213> ORGANISM: Artificial Sequence
<220> FEATURE:
<223> OTHER INFORMATION: A12722 sdAb sequence

<400> SEQUENCE: 34

Gln Val Lys Leu Glu Glu Ser Gly Gly Gly Leu Val Gln Ala Gly Gly
1               5                   10                  15

Ser Leu Arg Leu Ser Cys Val Ala Ser Gly Ser Gly Phe Gly Ile Asn
            20                  25                  30

Gly Val Ile Trp Tyr Arg Gln Ala Pro Gly Lys Gln Arg Glu Leu Val
        35                  40                  45

Ala Leu Ile Lys Ser Asp Gly Tyr Thr Asn Tyr Arg Glu Ser Val Lys
    50                  55                  60

Gly Arg Phe Thr Ile Ser Arg Asp Asp Ala Lys Asn Thr Val Trp Leu
65                  70                  75                  80

Gln Met Asn Ala Leu Glu Pro Glu Asp Thr Gly Val Tyr Tyr Cys Lys
                85                  90                  95

Thr Pro Gly Val Pro Phe Gly Gln Gly Thr Pro Val Thr Val Ser Ser
            100                 105                 110

<210> SEQ ID NO 35
<211> LENGTH: 336
<212> TYPE: DNA
<213> ORGANISM: Artificial Sequence
<220> FEATURE:
<223> OTHER INFORMATION: nucleotide sequence encoding A12680 sdAb

<400> SEQUENCE: 35

```
caggtaaagc tggaggagtc tgggggaggc ttggtgcagg ctggggggtc tctgagactc        60
tcctgtgtag cctcgggaag cggcttcggg atcaatggcg tgatctggta tcgccaggct       120
ccagggaagc agcgcgagtt ggtcgcgctt attaagagtg acggttatac aaattataga       180
gagtccgtga aggccgatt caccatctcc agagacgacg ccaagaacac ggtgtggctg        240
caaatgaacg ccctggaacc tgaggacaca ggcgtctatt actgtaaaac acccggagta       300
ccgtttggtc aggggaccca ggtcaccgtc tcctca                                 336
```

<210> SEQ ID NO 36

```
<211> LENGTH: 112
<212> TYPE: PRT
<213> ORGANISM: Artificial Sequence
<220> FEATURE:
<223> OTHER INFORMATION: A12680 sdAb sequence

<400> SEQUENCE: 36

Gln Val Lys Leu Glu Glu Ser Gly Gly Gly Leu Val Gln Ala Gly Gly
1               5                   10                  15

Ser Leu Arg Leu Ser Cys Val Ala Ser Gly Ser Gly Phe Gly Ile Asn
            20                  25                  30

Gly Val Ile Trp Tyr Arg Gln Ala Pro Gly Lys Gln Arg Glu Leu Val
        35                  40                  45

Ala Leu Ile Lys Ser Asp Gly Tyr Thr Asn Tyr Arg Glu Ser Val Lys
    50                  55                  60

Gly Arg Phe Thr Ile Ser Arg Asp Asp Ala Lys Asn Thr Val Trp Leu
65                  70                  75                  80

Gln Met Asn Ala Leu Glu Pro Glu Asp Thr Gly Val Tyr Tyr Cys Lys
                85                  90                  95

Thr Pro Gly Val Pro Phe Gly Gln Gly Thr Gln Val Thr Val Ser Ser
            100                 105                 110

<210> SEQ ID NO 37
<211> LENGTH: 336
<212> TYPE: DNA
<213> ORGANISM: Artificial Sequence
<220> FEATURE:
<223> OTHER INFORMATION: nucleotide sequence encoding A12690 sdAb

<400> SEQUENCE: 37
caggtacagc tggtggagtc tgggggaggc ttggtgcagc ctggggggtc tctgagactc      60
tcctgtgtag cctcgggaag cggcttcggg atcaatggcg tgatctggta tcgccaggct     120
ccagggaagc ggcgcgagtt ggtcgcgctt attaagagtg acggttatac aaattataga     180
gagtccgtga agggccgatt caccatctcc agagacgacg ccaagaacac ggtgtggctg     240
caaatgaacg ccctggaacc tgaggacaca ggcgtctatt actgtaaaac acccggagta     300
ccgtttggtc aggggaccca ggtcaccgtc tcctca                               336

<210> SEQ ID NO 38
<211> LENGTH: 112
<212> TYPE: PRT
<213> ORGANISM: Artificial Sequence
<220> FEATURE:
<223> OTHER INFORMATION: A12690 sdAb sequence

<400> SEQUENCE: 38

Gln Val Gln Leu Val Glu Ser Gly Gly Gly Leu Val Gln Pro Gly Gly
1               5                   10                  15

Ser Leu Arg Leu Ser Cys Val Ala Ser Gly Ser Gly Phe Gly Ile Asn
            20                  25                  30

Gly Val Ile Trp Tyr Arg Gln Ala Pro Gly Lys Arg Arg Glu Leu Val
        35                  40                  45

Ala Leu Ile Lys Ser Asp Gly Tyr Thr Asn Tyr Arg Glu Ser Val Lys
    50                  55                  60

Gly Arg Phe Thr Ile Ser Arg Asp Asp Ala Lys Asn Thr Val Trp Leu
65                  70                  75                  80

Gln Met Asn Ala Leu Glu Pro Glu Asp Thr Gly Val Tyr Tyr Cys Lys
                85                  90                  95
```

```
Thr Pro Gly Val Pro Phe Gly Gln Gly Thr Gln Val Thr Val Ser Ser
            100                 105                 110
```

<210> SEQ ID NO 39
<211> LENGTH: 336
<212> TYPE: DNA
<213> ORGANISM: Artificial Sequence
<220> FEATURE:
<223> OTHER INFORMATION: nucleotide sequence encoding A13154 sdAb

<400> SEQUENCE: 39

```
caggtacagc tggtggagtc tggggggaggc ttggtgcagc ctggggggtc tctgagactc      60
tcctgtgtag cctcgggaag cggcttcggg atcaatggcg tgatctggta tcgccaggct     120
ccagggaagc agcgcgagtt ggtcgcgctt attaagagtg acggttatac aaattataga     180
gagtccgtga aggccgatt caccatctcc agagacgacg ccaagaacac ggtgtggctg      240
caaatgagcg ccctggaacc tgaggacaca ggcgtctatt actgtaaaac acccggagta     300
ccgtttggtc aggggaccca ggtcaccgtc tcctca                               336
```

<210> SEQ ID NO 40
<211> LENGTH: 112
<212> TYPE: PRT
<213> ORGANISM: Artificial Sequence
<220> FEATURE:
<223> OTHER INFORMATION: A13154 sdAb sequence

<400> SEQUENCE: 40

```
Gln Val Gln Leu Val Glu Ser Gly Gly Gly Leu Val Gln Pro Gly Gly
1               5                   10                  15

Ser Leu Arg Leu Ser Cys Val Ala Ser Gly Ser Gly Phe Gly Ile Asn
            20                  25                  30

Gly Val Ile Trp Tyr Arg Gln Ala Pro Gly Lys Gln Arg Glu Leu Val
        35                  40                  45

Ala Leu Ile Lys Ser Asp Gly Tyr Thr Asn Tyr Arg Glu Ser Val Lys
    50                  55                  60

Gly Arg Phe Thr Ile Ser Arg Asp Asp Ala Lys Asn Thr Val Trp Leu
65                  70                  75                  80

Gln Met Ser Ala Leu Glu Pro Glu Asp Thr Gly Val Tyr Tyr Cys Lys
                85                  90                  95

Thr Pro Gly Val Pro Phe Gly Gln Gly Thr Gln Val Thr Val Ser Ser
            100                 105                 110
```

<210> SEQ ID NO 41
<211> LENGTH: 336
<212> TYPE: DNA
<213> ORGANISM: Artificial Sequence
<220> FEATURE:
<223> OTHER INFORMATION: nucleotide sequence encoding A13146 sdAb

<400> SEQUENCE: 41

```
gctgtacagc tggtggattc tggggggaggc ttggtgcagg ctggggggtc tctgagactc      60
tcctgtgtag cctcgggaag cggcttcggg atcaatggcg tgatctggta tcgccaggct     120
ccagggaagc agcgcgagtt ggtcgcgctt attaagagtg acggttatac aaattataga     180
gagtccgtga aggccgatt caccatctcc agagacgacg ccaagaacac ggtgtggctg      240
caaatgaacg ccctggaacc tgaggacaca ggcgtctatt actgtaaaac acccggagta     300
ccgtttggtc aggggaccca ggtcaccgtc tcctca                               336
```

<210> SEQ ID NO 42
<211> LENGTH: 112
<212> TYPE: PRT
<213> ORGANISM: Artificial Sequence
<220> FEATURE:
<223> OTHER INFORMATION: A13146 sdAb sequence

<400> SEQUENCE: 42

```
Ala Val Gln Leu Val Asp Ser Gly Gly Gly Leu Val Gln Ala Gly Gly
1               5                   10                  15
Ser Leu Arg Leu Ser Cys Val Ala Gly Ser Gly Phe Gly Ile Asn
            20                  25                  30
Gly Val Ile Trp Tyr Arg Gln Ala Pro Gly Lys Gln Arg Glu Leu Val
        35                  40                  45
Ala Leu Ile Lys Ser Asp Gly Tyr Thr Asn Tyr Arg Glu Ser Val Lys
    50                  55                  60
Gly Arg Phe Thr Ile Ser Arg Asp Asp Ala Lys Asn Thr Val Trp Leu
65                  70                  75                  80
Gln Met Asn Ala Leu Glu Pro Glu Asp Thr Gly Val Tyr Tyr Cys Lys
                85                  90                  95
Thr Pro Gly Val Pro Phe Gly Gln Gly Thr Gln Val Thr Val Ser Ser
            100                 105                 110
```

<210> SEQ ID NO 43
<211> LENGTH: 336
<212> TYPE: DNA
<213> ORGANISM: Artificial Sequence
<220> FEATURE:
<223> OTHER INFORMATION: nucleotide sequence encoding A13149 sdAb

<400> SEQUENCE: 43

```
caggtacagc tggtggagtc tgggggaggc ttggtgcagc ctgggggggtc tctgagactc    60
tcctgtgtag cctcgggaag cggcttcggg atcaatggcg tgatctggta tcgccaggct   120
ccagggaagc agcgcgagtt ggtcgcgctt attaagagtg acggttatac aaattataga   180
gagtccgtga agggccgatt caccatctcc agagacgacg ccaagaacac ggtgtggctg   240
caaatgaacg ccctggaacc tgaggacaca ggcgtctatt actgtaaaac acccggagta   300
ccgtttggtc aggggaccca ggtcaccgtc tcctca                             336
```

<210> SEQ ID NO 44
<211> LENGTH: 112
<212> TYPE: PRT
<213> ORGANISM: Artificial Sequence
<220> FEATURE:
<223> OTHER INFORMATION: A13149 sdAb sequence

<400> SEQUENCE: 44

```
Gln Val Gln Leu Val Glu Ser Gly Gly Gly Leu Val Gln Pro Gly Gly
1               5                   10                  15
Ser Leu Arg Leu Ser Cys Val Ala Ser Gly Ser Gly Phe Gly Ile Asn
            20                  25                  30
Gly Val Ile Trp Tyr Arg Gln Ala Pro Gly Lys Gln Arg Glu Leu Val
        35                  40                  45
Ala Leu Ile Lys Ser Asp Gly Tyr Thr Asn Tyr Arg Glu Ser Val Lys
    50                  55                  60
Gly Arg Phe Thr Ile Ser Arg Asp Asp Ala Lys Asn Thr Val Trp Leu
65                  70                  75                  80
Gln Met Asn Ala Leu Glu Pro Glu Asp Thr Gly Val Tyr Tyr Cys Lys
                85                  90                  95
```

Thr Pro Gly Val Pro Phe Gly Gln Gly Thr Gln Val Thr Val Ser Ser
         100                 105                 110

<210> SEQ ID NO 45
<211> LENGTH: 336
<212> TYPE: DNA
<213> ORGANISM: Artificial Sequence
<220> FEATURE:
<223> OTHER INFORMATION: nucleotide sequence encoding A12666 sdAb

<400> SEQUENCE: 45
caggtaaagc tggaggagtc tgggggaggc ttggtgcagg ctggggggtc tctgagactc      60
tcctgtgtag cctcgggaag cggcttcggg gtcaatggcg tgatctggta tcgccaggct     120
ccagggaagc agcgcgagtt ggtcgcgctt attaagagtg acggttatac aaattataga     180
gagtccgtga agggccgatt caccatctcc agagacgacg ccaagaacac ggtgtggctg     240
caaatgaacg ccctggaacc tgaggacaca ggcgtctatt actgtaaaac acccggagta     300
ccgtttggtc aggggaccca ggtcaccgtc tcctca                               336

<210> SEQ ID NO 46
<211> LENGTH: 112
<212> TYPE: PRT
<213> ORGANISM: Artificial Sequence
<220> FEATURE:
<223> OTHER INFORMATION: A12666 sdAb sequence

<400> SEQUENCE: 46

Gln Val Lys Leu Glu Glu Ser Gly Gly Gly Leu Val Gln Ala Gly Gly
1               5                   10                  15

Ser Leu Arg Leu Ser Cys Val Ala Ser Gly Ser Gly Phe Gly Val Asn
            20                  25                  30

Gly Val Ile Trp Tyr Arg Gln Ala Pro Gly Lys Gln Arg Glu Leu Val
        35                  40                  45

Ala Leu Ile Lys Ser Asp Gly Tyr Thr Asn Tyr Arg Glu Ser Val Lys
    50                  55                  60

Gly Arg Phe Thr Ile Ser Arg Asp Asp Ala Lys Asn Thr Val Trp Leu
65                  70                  75                  80

Gln Met Asn Ala Leu Glu Pro Glu Asp Thr Gly Val Tyr Tyr Cys Lys
                85                  90                  95

Thr Pro Gly Val Pro Phe Gly Gln Gly Thr Gln Val Thr Val Ser Ser
            100                 105                 110

<210> SEQ ID NO 47
<211> LENGTH: 336
<212> TYPE: DNA
<213> ORGANISM: Artificial Sequence
<220> FEATURE:
<223> OTHER INFORMATION: nucleotide sequence encoding A12659 sdAb

<400> SEQUENCE: 47
gaggtgcagc tggtggagtg tgggggaggc ttggtgcagg ctggggggtc tctgagactc      60
tcctgtgtag cctcgggaag cggcttcggg atcaatggcg tgatctggta tcgccaggct     120
ccagggaagc agcgcgagtt ggtcgcgctt attaagagtg acggttatac aaattataga     180
gagtccgtga agggccgatt caccatctcc agagacgacg ccaggaacac ggtgtggctg     240
caaatgaacg ccctggaacc tgaggacaca ggcgtctatt actgtaaaac acccggagta     300
ccgtttggtc aggggaccca ggtcaccgtc tcctca                               336

<210> SEQ ID NO 48
<211> LENGTH: 112
<212> TYPE: PRT
<213> ORGANISM: Artificial Sequence
<220> FEATURE:
<223> OTHER INFORMATION: A12659 sdAb sequence

<400> SEQUENCE: 48

```
Glu Val Gln Leu Val Glu Cys Gly Gly Gly Leu Val Gln Ala Gly
1               5                   10                  15

Ser Leu Arg Leu Ser Cys Val Ala Ser Gly Ser Gly Phe Gly Ile Asn
            20                  25                  30

Gly Val Ile Trp Tyr Arg Gln Ala Pro Gly Lys Gln Arg Glu Leu Val
        35                  40                  45

Ala Leu Ile Lys Ser Asp Gly Tyr Thr Asn Tyr Arg Glu Ser Val Lys
    50                  55                  60

Gly Arg Phe Thr Ile Ser Arg Asp Asp Ala Arg Asn Thr Val Trp Leu
65                  70                  75                  80

Gln Met Asn Ala Leu Glu Pro Glu Asp Thr Gly Val Tyr Tyr Cys Lys
                85                  90                  95

Thr Pro Gly Val Pro Phe Gly Gly Thr Gln Val Thr Val Ser Ser
            100                 105                 110
```

<210> SEQ ID NO 49
<211> LENGTH: 336
<212> TYPE: DNA
<213> ORGANISM: Artificial Sequence
<220> FEATURE:
<223> OTHER INFORMATION: nucleotide sequence encoding A13355 sdAb

<400> SEQUENCE: 49

```
caggtaaagc tggaggagtc tgggggaggc ttggtgcagg ctggggggtc tctgagactc      60
tcctgtgtgg cctcgggaag cggcttcggg atcaatggcg tgatctggta tcgccaggct    120
ccagggaagc agcgcgagtt ggtcgcgctt attaagagtg acggttatac aaattatagg    180
gagtccgtga gggccgatt caccatctcc agagacgacg ccaagaacac ggtgtggctg    240
caaatgaacg ccctggaacc tgaggacaca ggcgtctatt actgtaaaac acccggagta    300
ccgtttggtc aggggaccca ggtcaccgtc tcctca                             336
```

<210> SEQ ID NO 50
<211> LENGTH: 112
<212> TYPE: PRT
<213> ORGANISM: Artificial Sequence
<220> FEATURE:
<223> OTHER INFORMATION: A13355 sdAb sequence

<400> SEQUENCE: 50

```
Gln Val Lys Leu Glu Glu Ser Gly Gly Gly Leu Val Gln Ala Gly Gly
1               5                   10                  15

Ser Leu Arg Leu Ser Cys Val Ala Ser Gly Ser Gly Phe Gly Ile Asn
            20                  25                  30

Gly Val Ile Trp Tyr Arg Gln Ala Pro Gly Lys Gln Arg Glu Leu Val
        35                  40                  45

Ala Leu Ile Lys Ser Asp Gly Tyr Thr Asn Tyr Arg Glu Ser Val Arg
    50                  55                  60

Gly Arg Phe Thr Ile Ser Arg Asp Asp Ala Lys Asn Thr Val Trp Leu
65                  70                  75                  80

Gln Met Asn Ala Leu Glu Pro Glu Asp Thr Gly Val Tyr Tyr Cys Lys
```

```
                      85                  90                  95

Thr Pro Gly Val Pro Phe Gly Gln Gly Thr Gln Val Thr Val Ser Ser
            100                 105                 110

<210> SEQ ID NO 51
<211> LENGTH: 336
<212> TYPE: DNA
<213> ORGANISM: Artificial Sequence
<220> FEATURE:
<223> OTHER INFORMATION: nucleotide sequence encoding A12692 sdAb

<400> SEQUENCE: 51
gaggtgcagc tggtggagtg tgggggaggc ttggtgcagg ctgggggtc tctgagactc      60 tcctgtgtag cctcgggaag cggcttcggg atcaatggcg tgatctggta tcgccaggct     120
ccagggaagc agcgcgagtt ggtcgcgctt attaagagtg acggttatac aaattataga     180
gagtccgtga agggccgatt caccatctcc agagacgacg ccaagaacac ggtgtggctg     240
caaatgaacg ccctggaacc tgaggacaca ggcgtctatt actgtaaaac acccggagta     300
ccgtttggtc aggggaccca ggtcaccgtc tcctca                              336

<210> SEQ ID NO 52
<211> LENGTH: 112
<212> TYPE: PRT
<213> ORGANISM: Artificial Sequence
<220> FEATURE:
<223> OTHER INFORMATION: A12692 sdAb sequence

<400> SEQUENCE: 52

Glu Val Gln Leu Val Glu Cys Gly Gly Gly Leu Val Gln Ala Gly Gly
1               5                   10                  15

Ser Leu Arg Leu Ser Cys Val Ala Ser Gly Ser Gly Phe Gly Ile Asn
            20                  25                  30

Gly Val Ile Trp Tyr Arg Gln Ala Pro Gly Lys Gln Arg Glu Leu Val
        35                  40                  45

Ala Leu Ile Lys Ser Asp Gly Tyr Thr Asn Tyr Arg Glu Ser Val Lys
    50                  55                  60

Gly Arg Phe Thr Ile Ser Arg Asp Asp Ala Lys Asn Thr Val Trp Leu
65                  70                  75                  80

Gln Met Asn Ala Leu Glu Pro Glu Asp Thr Gly Val Tyr Tyr Cys Lys
                85                  90                  95

Thr Pro Gly Val Pro Phe Gly Gln Gly Thr Gln Val Thr Val Ser Ser
            100                 105                 110

<210> SEQ ID NO 53
<211> LENGTH: 366
<212> TYPE: DNA
<213> ORGANISM: Artificial Sequence
<220> FEATURE:
<223> OTHER INFORMATION: nucleotide sequence encoding A69476 sdAb

<400> SEQUENCE: 53
caggtaaagc tggaggagtc tgggggaggc ttggtgcagc ctgggggtc tctgagactc      60 tcctgtgcag cctctggaaa cgtcttcact atcgatgcca tggctgta ccgccaggct      120 cctggaaagg agcgcgaagt cgtcgtagga atgacaaacg gtggtaaaac gaactatgca     180
gactccgtga agggccgatt caccatctcc agagacaacg ccaagaacac ggtgtcgctg     240
caaatgaaca gcctgaaacc tgaggacaca gccgtctatt attgttatgc tcgtagtaaa     300
cttatagcga ctataaacaa cccgtatgac tactgggggcc aggggaccca ggtcaccgtc    360
``` tcctca 366

<210> SEQ ID NO 54
<211> LENGTH: 122
<212> TYPE: PRT
<213> ORGANISM: Artificial Sequence
<220> FEATURE:
<223> OTHER INFORMATION: A69476 sdAb sequence

<400> SEQUENCE: 54

```
Gln Val Lys Leu Glu Glu Ser Gly Gly Gly Leu Val Gln Pro Gly Gly
1               5                   10                  15
Ser Leu Arg Leu Ser Cys Ala Ala Ser Gly Asn Val Phe Thr Ile Asp
            20                  25                  30
Ala Met Gly Trp Tyr Arg Gln Ala Pro Gly Lys Glu Arg Glu Val Val
        35                  40                  45
Val Gly Met Thr Asn Gly Gly Lys Thr Asn Tyr Ala Asp Ser Val Lys
    50                  55                  60
Gly Arg Phe Thr Ile Ser Arg Asp Asn Ala Lys Asn Thr Val Ser Leu
65                  70                  75                  80
Gln Met Asn Ser Leu Lys Pro Glu Asp Thr Ala Val Tyr Tyr Cys Tyr
                85                  90                  95
Ala Arg Ser Lys Leu Ile Ala Thr Ile Asn Asn Pro Tyr Asp Tyr Trp
            100                 105                 110
Gly Gln Gly Thr Gln Val Thr Val Ser Ser
        115                 120
```

<210> SEQ ID NO 55
<211> LENGTH: 366
<212> TYPE: DNA
<213> ORGANISM: Artificial Sequence
<220> FEATURE:
<223> OTHER INFORMATION: nucleotide sequence encoding A69449 sdAb

<400> SEQUENCE: 55
caggtacagc tggtggagtc tgggggaggc gtggtgcagg ctggggggtc tctgagactc    60
tcctgtgtag cctccggaag cgtcttcagt atcgacgcca tggctggta ccgccaggct    120 ccagggaacc agcgcgagtt ggtcgcggct atgactaatg ctggtagcac aaattatgca    180
gactccgtga aggccgatt caccatctcc agagacaacg ccgagaacac ggtgtatctg    240
caaatgaaca gcctgaaacc tgaggacaca gccgtctatt actgtaatgc gcgttctaaa    300
cttatagcgc gcatcaacaa cccgtatgaa tactggggcc aggggaccca ggtcaccgtc    360
tcctca    366

<210> SEQ ID NO 56
<211> LENGTH: 122
<212> TYPE: PRT
<213> ORGANISM: Artificial Sequence
<220> FEATURE:
<223> OTHER INFORMATION: A69449 sdAb sequence

<400> SEQUENCE: 56

```
Gln Val Gln Leu Val Glu Ser Gly Gly Gly Val Val Gln Ala Gly Gly
1               5                   10                  15
Ser Leu Arg Leu Ser Cys Val Ala Ser Gly Ser Val Phe Ser Ile Asp
            20                  25                  30
Ala Met Gly Trp Tyr Arg Gln Ala Pro Gly Asn Gln Arg Glu Leu Val
        35                  40                  45
```

Ala Ala Met Thr Asn Ala Gly Ser Thr Asn Tyr Ala Asp Ser Val Lys
         50                  55                  60

Gly Arg Phe Thr Ile Ser Arg Asp Asn Ala Glu Asn Thr Val Tyr Leu
 65                  70                  75                  80

Gln Met Asn Ser Leu Lys Pro Glu Asp Thr Ala Val Tyr Tyr Cys Asn
                 85                  90                  95

Ala Arg Ser Lys Leu Ile Ala Arg Ile Asn Asn Pro Tyr Glu Tyr Trp
            100                 105                 110

Gly Gln Gly Thr Gln Val Thr Val Ser Ser
            115                 120

<210> SEQ ID NO 57
<211> LENGTH: 363
<212> TYPE: DNA
<213> ORGANISM: Artificial Sequence
<220> FEATURE:
<223> OTHER INFORMATION: nucleotide sequence encoding A69433 sdAb

<400> SEQUENCE: 57
caggtaaagc tggaggagtc tgggggaggc ttggtgcagg ctggcgggtc tctgagactc      60
tcctgtgtag cctctggaaa cgtcttcggt atcgatgccg tgggctggta ccgccaggct     120
ccagggaagc agcgcgagtt ggtcgcagct actactacta gcggtagtag cacaaactat     180
gcagactccg tgaagggccg attcaccatc tccaggaca tcgccaagaa cacggtgtat     240
ctgcaaatgg acagcctgaa acctgaggac acagccgtct attattgtta tgcccgccct     300
aagcaagcga ctctgattcg ggatgattac tggggccagg gacccaggt caccgtctcc     360 tca                                                                  363

<210> SEQ ID NO 58
<211> LENGTH: 121
<212> TYPE: PRT
<213> ORGANISM: Artificial Sequence
<220> FEATURE:
<223> OTHER INFORMATION: A69433 sdAb sequence

<400> SEQUENCE: 58

Gln Val Lys Leu Glu Glu Ser Gly Gly Gly Leu Val Gln Ala Gly Gly
  1               5                  10                  15

Ser Leu Arg Leu Ser Cys Val Ala Ser Gly Asn Val Phe Gly Ile Asp
             20                  25                  30

Ala Val Gly Trp Tyr Arg Gln Ala Pro Gly Lys Gln Arg Glu Leu Val
         35                  40                  45

Ala Ala Thr Thr Thr Ser Gly Ser Ser Thr Asn Tyr Ala Asp Ser Val
     50                  55                  60

Lys Gly Arg Phe Thr Ile Ser Arg Asp Ile Ala Lys Asn Thr Val Tyr
 65                  70                  75                  80

Leu Gln Met Asp Ser Leu Lys Pro Glu Asp Thr Ala Val Tyr Tyr Cys
                 85                  90                  95

Tyr Ala Arg Pro Lys Gln Ala Thr Leu Ile Arg Asp Asp Tyr Trp Gly
            100                 105                 110

Gln Gly Thr Gln Val Thr Val Ser Ser
            115                 120

<210> SEQ ID NO 59
<211> LENGTH: 363
<212> TYPE: DNA
<213> ORGANISM: Artificial Sequence
<220> FEATURE:
<223> OTHER INFORMATION: nucleotide sequence encoding A69441 sdAb

<400> SEQUENCE: 59

```
caggtaaagc tggaggagtc tgggggaggc ttggtgcagc ctggggggtc tctgagactc    60
tcctgtgcag cctctggaag catcttcagt atcaaggtca tgggctggta ccgccaggct   120
ccagggaagc agcgcgagtt ggtcgcagat attactagtg gtggtagtac agactattca   180
gactccgtga agggccgatt caccatctcc agagacaacg ccaagaacac ggtgtatctg   240
caaatgaaca gcctgaaacc tgaggacacg gccgtctatt actgtaatgc agatttgggc   300
tgctcaggcg ctgggtcctg ccctgactac tggggccagg ggacccaggt caccgtctcc   360
tca                                                                 363
```

<210> SEQ ID NO 60
<211> LENGTH: 121
<212> TYPE: PRT
<213> ORGANISM: Artificial Sequence
<220> FEATURE:
<223> OTHER INFORMATION: A69441 sdAb sequence

<400> SEQUENCE: 60

Gln Val Lys Leu Glu Glu Ser Gly Gly Gly Leu Val Gln Pro Gly Gly
1               5                   10                  15
Ser Leu Arg Leu Ser Cys Ala Ala Ser Gly Ser Ile Phe Ser Ile Lys
            20                  25                  30
Val Met Gly Trp Tyr Arg Gln Ala Pro Gly Lys Gln Arg Glu Leu Val
        35                  40                  45
Ala Asp Ile Thr Ser Gly Gly Ser Thr Asp Tyr Ser Asp Ser Val Lys
    50                  55                  60
Gly Arg Phe Thr Ile Ser Arg Asp Asn Ala Lys Asn Thr Val Tyr Leu
65                  70                  75                  80
Gln Met Asn Ser Leu Lys Pro Glu Asp Thr Ala Val Tyr Tyr Cys Asn
                85                  90                  95
Ala Asp Leu Gly Cys Ser Gly Ala Gly Ser Cys Pro Asp Tyr Trp Gly
            100                 105                 110
Gln Gly Thr Gln Val Thr Val Ser Ser
        115                 120

<210> SEQ ID NO 61
<211> LENGTH: 351
<212> TYPE: DNA
<213> ORGANISM: Artificial Sequence
<220> FEATURE:
<223> OTHER INFORMATION: nucleotide sequence encoding A69447 sdAb

<400> SEQUENCE: 61

```
caggtaaagc tggaggagtc tgggggaggc tcggtgcagg ctggggggtc tctgagactc    60
tcctgtacag gctcgggaag catcttccca ttgaatgaca tgggctggta ccgccaggct   120
cctgggaagc agcgcgagtt ggtcgctaca attactaggg gcggcactac aaattatgca   180
gactccgtga agggccgatt caccatctcc agagacagca acgccaagaa cacggtgtat   240
ctgcaaatga acagcctgaa agtagaggat acagccgtct attactgtaa tatggataat   300
cgagtaggtg gcagttactg ggggccaggg acccaggtca ccgtctcctc a            351
```

<210> SEQ ID NO 62
<211> LENGTH: 117
<212> TYPE: PRT

<213> ORGANISM: Artificial Sequence
<220> FEATURE:
<223> OTHER INFORMATION: A69447 sdAb sequence

<400> SEQUENCE: 62

Gln Val Lys Leu Glu Glu Ser Gly Gly Gly Ser Val Gln Ala Gly Gly
1               5                   10                  15

Ser Leu Arg Leu Ser Cys Thr Gly Ser Gly Ser Ile Phe Pro Leu Asn
            20                  25                  30

Asp Met Gly Trp Tyr Arg Gln Ala Pro Gly Lys Gln Arg Glu Leu Val
        35                  40                  45

Ala Thr Ile Thr Arg Gly Gly Thr Thr Asn Tyr Ala Asp Ser Val Lys
    50                  55                  60

Gly Arg Phe Thr Ile Ser Arg Asp Ser Asn Ala Lys Asn Thr Val Tyr
65                  70                  75                  80

Leu Gln Met Asn Ser Leu Lys Val Glu Asp Thr Ala Val Tyr Tyr Cys
                85                  90                  95

Asn Met Asp Asn Arg Val Gly Ser Tyr Trp Gly Gln Gly Thr Gln
            100                 105                 110

Val Thr Val Ser Ser
        115

<210> SEQ ID NO 63
<211> LENGTH: 45
<212> TYPE: DNA
<213> ORGANISM: Artificial Sequence
<220> FEATURE:
<223> OTHER INFORMATION: P441_VHHF1 forward primer sequence

<400> SEQUENCE: 63
gcccagccgg ccatggccsm bgtrcagctg gtggaktctg gggga          45

<210> SEQ ID NO 64
<211> LENGTH: 45
<212> TYPE: DNA
<213> ORGANISM: Artificial Sequence
<220> FEATURE:
<223> OTHER INFORMATION: P442_VHHF2 forward primer sequence

<400> SEQUENCE: 64
gcccagccgg ccatggccca ggtaaagctg gaggagtctg gggga          45

<210> SEQ ID NO 65
<211> LENGTH: 39
<212> TYPE: DNA
<213> ORGANISM: Artificial Sequence
<220> FEATURE:
<223> OTHER INFORMATION: P759_VHHF3 forward primer sequence

<400> SEQUENCE: 65
gcccagccgg ccatggccca ggtacagctg gtggagtct                 39

<210> SEQ ID NO 66
<211> LENGTH: 41
<212> TYPE: DNA
<213> ORGANISM: Artificial Sequence
<220> FEATURE:
<223> OTHER INFORMATION: P444_VHHF4 forward primer sequence

<400> SEQUENCE: 66
gcccagccgg ccatggccga ggtgcagctg gtggagtgtg g              41

```
<210> SEQ ID NO 67
<211> LENGTH: 21
<212> TYPE: DNA
<213> ORGANISM: Artificial Sequence
<220> FEATURE:
<223> OTHER INFORMATION: P445_CH2R  reverse primer sequence

<400> SEQUENCE: 67
cgccatcaag gtaccagttg a                                               21

<210> SEQ ID NO 68
<211> LENGTH: 29
<212> TYPE: DNA
<213> ORGANISM: Artificial Sequence
<220> FEATURE:
<223> OTHER INFORMATION: P446_CH2b3R  reverse primer sequence

<400> SEQUENCE: 68
ggggtacctg tcatccacgg accagctga                                       29

<210> SEQ ID NO 69
<211> LENGTH: 34
<212> TYPE: DNA
<213> ORGANISM: Artificial Sequence
<220> FEATURE:
<223> OTHER INFORMATION: P440_VHHF forward primer sequence

<400> SEQUENCE: 69
catgtgtaga ctcgcggccc agccggccat ggcc                                 34

<210> SEQ ID NO 70
<211> LENGTH: 46
<212> TYPE: DNA
<213> ORGANISM: Artificial Sequence
<220> FEATURE:
<223> OTHER INFORMATION: P447_VHHR reverse primer sequence

<400> SEQUENCE: 70
catgtgtaga ttcctggccg gcctggcctg aggagacggt gacctg                    46
```

COMPOSITIONS AND METHODS FOR INCREASING PROTEIN HALF-LIFE IN A SERUM

CROSS REFERENCE TO RELATED APPLICATION

This application is a divisional of U.S. application Ser. No. 14/903,156, filed Jan. 6, 2016, which is a Section 371 of International Application No. PCT/US14/45768, filed Jul. 8, 2014, which was published Jan. 15, 2015 under International Publication No. WO 2015/006337 A2, which claims priority to U.S. Provisional Patent Application No. 61/843,628, filed Jul. 8, 2013, the discloses of which are incorporated herein by reference.

REFERENCE TO SEQUENCE LISTING SUBMITTED ELECTRONICALLY

This application contains a sequence listing, which is submitted electronically via EFS-Web as an ASCII formatted sequence listing with a file name "689296-2U2 Sequence Listing," creation date of May 14, 2019, and having a size of 40.9 kb. The sequence listing submitted via EFS-Web is part of the specification and is herein incorporated by reference in its entirety.

BACKGROUND OF THE INVENTION

Pharmacokinetics of a drug candidate is a critical parameter and often largely determines whether or not the drug candidate will be further developed into a drug or used for a therapeutic application. In particular, pharmacokinetic studies of protein- and peptide-based therapeutics, including antibodies, have demonstrated that such therapeutics have varying serum half lives, and those peptides and proteins with a short serum half-life, although having a promising therapeutic potential, are thus often unsuitable for further drug development. For example, albumin and gamma immunoglobulins (IgGs) are known to have very long serum half lives of up to 20 days [1]. In addition, the Fc domain of other IgGs can be engineered to alter their binding interactions to neonatal Fc receptor as a method of prolonging serum half-life [2]. However, many other natural human proteins, such as insulin, antibody fragments such as antigen binding fragments (Fabs) or single chain variable fragment (scFvs), and short peptides usually have much shorter serum half-lives ranging from minutes to approximately only 1 hour. An efficient, cost effective and safe way of extending serum half lives of proteins and peptides with short half-lives is therefore critical for these molecules to become therapeutic drugs, diagnostic tools, etc.

Several strategies have been developed in an effort to prolong the serum half-life of proteins and other peptidic molecules that are short-lived in serum to avoid clearance of such therapeutic or diagnostic proteins from circulation. Several technologies employed to facilitate serum half-life extension of proteins and peptidic molecules include conjugation with a chemical attachment such as polyethylene glycol (i.e. pegylation) [3], fusion to the Fc region of an antibody [4], and fusion to a protein naturally having a long serum half life, such as albumin [5]. Unfortunately, these technologies suffer from complications including complex manufacturing and characterization processes, low expression levels, and undesired functions of the generated molecules.

Another approach that has been more recently developed to extend the serum half-life of proteins and other peptidic molecules employs the use of antibody fragments against serum proteins. Albumin, due mainly to its high serum concentration and long serum half-life, has been the most selected target for this purpose. An isolated domain antibody against human albumin was shown to prolong the serum half-life of interferon (IFN)-α2b after the two molecules were fused at the genetic level and expressed as a fusion protein [6, 7]. The serum half-life of the newly generated fusion protein molecule is not only longer than that of IFN-α2b, but even longer than that of the fusion protein of albumin and IFN-α2b.

Heavy chain variable domains of camelid heavy chain antibodies (HCAbs), known as VHH or single domain antibodies (sdAbs), have also been exploited for this purpose. For example, a sdAb against human albumin was shown to extend the serum half-life of an anti-TNFα sdAb fragment from less than one hour to over two days [8].

Another serum protein with a long half life is transferrin. Transferrin is a plasma glycoprotein that transfers iron ions and has a serum concentration of approximately 3 g/L and serum half-life of 7-8 days. Thus, transferrin is an ideal fusion partner to extend the serum half life of peptidic molecules with unsatisfactory pharmacokinetics. Studies have shown that fusion to transferrin significantly extended the serum half-life of both glucagon-like peptide 1 (GLP1) [9] and acetylcholine receptor [10].

However, the use of antibodies and antibody fragments such as sdAbs against transferrin, for increasing the serum half-life of peptidic molecules has not been reported. New methods for increasing the serum half-life of proteins and for producing proteins with improved serum half-life, that are efficient, cost-effective, and produce such proteins in high yield would facilitate the development of novel protein-based diagnostics or therapeutics. Embodiments of the present invention relate to such methods.

BRIEF SUMMARY OF THE INVENTION

The present invention relates to novel antibodies against transferrin, and particularly single domain antibodies (sdAbs) against transferrin. The present invention also relates to methods of using antibodies that specifically bind transferrin to increase the half-life of a target protein in the presence of the transferrin, novel fusion proteins comprising the target protein having an increased half-life in the presence of the transferrin, and compositions comprising the antibodies that specifically bind transferrin, or a fusion protein according to the invention.

In one general aspect, the present invention relates to an isolated antibody or fragment thereof that specifically binds a transferrin, the antibody or fragment thereof comprising one or more selected from the group consisting of:

(a) a complementarity determining region (CDR) 1 comprising an amino acid sequence selected from the group consisting of GSGFGINGVI (SEQ ID NO: 1); GSGFGVNGVI (SEQ ID NO: 2); GNVFTIAAMG (SEQ ID NO: 3); GNVFTIAAMA (SEQ ID NO: 4); GNVFTIDAMG (SEQ ID NO: 5); GSVFSIDAMG (SEQ ID NO: 6); GNVFGIDAVG (SEQ ID NO: 7); GSIFSIKVMG (SEQ ID NO: 8); and GSIFPLNDMG (SEQ ID NO: 9);

(b) a CDR2 comprising an amino acid sequence selected from the group consisting of LIKSDGYTNYRESVKG (SEQ ID NO: 10); LIKSDGYTNYRESVRG (SEQ ID NO: 11); GITTGGSTNYADSVKG (SEQ ID NO: 12);

GMTNGGKTNYADSVKG (SEQ ID NO: 13); AMTNAG-STNYADSVKG (SEQ ID NO: 14); ATTTSGSSTNY-ADSVKG (SEQ ID NO: 15); DITSGGSTDYSDSVKG (SEQ ID NO: 16); and TITRGGTTNYADSVKG (SEQ ID NO: 17); and
  (c) a CDR3 comprising an amino acid sequence selected from the group consisting of PGVP (SEQ ID NO: 18); VTKWAARVGGSAEYE (SEQ ID NO: 19); RSKLIA-TINNPYDY (SEQ ID NO: 20); RSKLIARINNPYEY (SEQ ID NO: 21); RPKQATLIRDDY (SEQ ID NO: 22); DLGCSGAGSCPDY (SEQ ID NO: 23); and DNRVGGSY (SEQ ID NO: 24).

Preferably, the antibody or fragment thereof is a single domain antibody (sdAb). More preferably, the antibody or antibody fragment thereof is an sdAb comprising the amino acid sequence of

A60219:
(SEQ ID NO: 26)
QVQLVESGGGLVQAGGSLRLSCVASGSGFGINGVIWYRQAPGKQRELVAL

IKSDGYTNYRESVKGRFTISRDDAKNTVWLQMNALEPEDTGVYYCKTPGV

PFGQGTQVTVSS;

A60401:
(SEQ ID NO: 28)
QVKLEESGGGLVQAGGSLRLSCEASGNVFTIAAMGWFRQAPGKERELVAG

ITTGGSTNYADSVKGRFTISRDNAQNTMYLQMNSLRPEDTAAYSCNAVTK

WAARVGGSAEYEWGQGTQVTVSS;

A69449:
(SEQ ID NO: 56)
QVQLVESGGGVVQAGGSLRLSCVASGSVFSIDAMGWYRQAPGNQRELVAA

MTNAGSTNYADSVKGRFTISRDNAENTVYLQMNSLKPEDTAVYYCNARSK

LIARINNPYEWGQGTQVTVSS;

A69433:
(SEQ ID NO: 58)
QVKLEESGGGLVQAGGSLRLSCVASGNVFGIDAVGWYRQAPGKQRELVAA

TTTSGSSTNYADSVKGRFTISRDIAKNTVYLQMDSLKPEDTAVYYCYARP

KQATLIRDDWGQGTQVTVSS;
or

A69447:
(SEQ ID NO: 62)
QVKLEESGGGSVQAGGSLRLSCTGSGSIFPLNDMGWYRQAPGKQRELVAT

ITRGGTTNYADSVKGRFTISRDSNAKNTVYLQMNSLKVEDTAVYYCNMDN

RVGGSYWGQGTQVTVSS.

The present invention also relates to a fusion protein comprising an antibody or fragment thereof according to embodiments of the present invention, a target protein, and optionally a linker, wherein the antibody or fragment thereof is fused to the carboxyl-terminus or amino-terminus of the target protein, and the linker optionally separates the antibody and the carboxyl-terminus or amino-terminus of the target protein.

The present invention also relates to a nucleic acid molecule comprising a cDNA or synthetic DNA encoding an antibody or fragment thereof according to embodiments of the present invention, or a nucleic acid encoding a fusion protein according to embodiments of the present invention, and related expression vectors and host cells.

In another general aspect, the present invention relates to a method for increasing the half-life of a target protein. According to embodiments of the invention, the method comprises:

(1) obtaining a fusion protein, wherein the fusion protein comprises an antibody or fragment thereof that specifically binds a transferrin, the target protein, and optionally a linker, wherein the antibody or fragment thereof is fused to a carboxyl-terminus or amino-terminus of the target protein, and the linker optionally separates the antibody and the carboxyl-terminus or amino-terminus of the target protein; and
(2) exposing the fusion protein to the transferrin to thereby increase the half-life of the target protein in the fusion protein compared to the target protein alone.

According to an embodiment of the present invention, the fusion protein is obtained by a method comprising:
  (a) obtaining an expression vector encoding the fusion protein;
  (b) introducing the expression vector into a cell to obtain a recombinant cell;
  (c) growing the recombinant cell under conditions to allow expression of the fusion protein; and
  (d) obtaining the fusion protein from the recombinant cell.

Another general aspect of the invention relates to a composition comprising an effective amount of a fusion protein, wherein the fusion protein comprises an antibody or fragment thereof that specifically binds a transferrin, a target protein, and optionally a linker, wherein the antibody or fragment thereof is fused to the carboxyl-terminus or amino-terminus of the target protein, and the linker optionally separates the antibody and the carboxyl-terminus or amino-terminus of the target protein. Preferably, the composition further comprises the transferrin.

The present invention also relates to a method comprising exposing a composition according to an embodiment of the present invention to the transferrin to thereby increase the half-life of the target protein in the fusion protein.

A further aspect of the present invention relates to a system for increasing the half-life of a target protein, the system comprising:
  (1) an expression vector comprising a first nucleotide sequence encoding an antibody or fragment thereof that specifically binds a transferrin, and optionally a second nucleotide sequence encoding a linker, wherein the first and second nucleotide sequences are operably linked,
  (2) a host cell, and
  (3) the transferrin.

Other aspects, features and advantages of the invention will be apparent from the following disclosure, including the detailed description of the invention and its preferred embodiments and the appended claims.

BRIEF DESCRIPTION OF THE DRAWINGS

The foregoing summary, as well as the following detailed description of the invention, will be better understood when read in conjunction with the appended drawings. For the purpose of illustrating the invention there are shown in the drawings embodiments which are presently preferred. It should be understood, however, that the invention is not limited to the precise arrangements and instrumentalities shown. In the drawings:

FIG. 2 is an alignment of the amino acid sequences of 19 isolated single domain antibodies (sdAbs) that bind human transferrin; complementarity determining regions (CDRs) and framework regions (FRs) are separated with a space; the sequences are numbered according to Kabat numbering; the sdAb sequences shown include A60219 (SEQ ID NO: 26), A13152 (SEQ ID NO: 30), A12722 (SEQ ID NO: 34), A12680 (SEQ ID NO: 36), A12690 (SEQ ID NO: 38), A13154 (SEQ ID NO: 40), A13146 (SEQ ID NO: 42), A13149 (SEQ ID NO: 44), A12666 (SEQ ID NO: 46), A12659 (SEQ ID NO: 48), A13355 (SEQ ID NO: 50), A12692 (SEQ ID NO: 52), A60401 (SEQ ID NO: 28), A13376 (SEQ ID NO: 32), A69476 (SEQ ID NO: 54), A69449 (SEQ ID NO: 56), A69433 (SEQ ID NO: 58), A69441 (SEQ ID NO: 60), and A69447 (SEQ ID NO: 62);

FIG. 4A shows SPR sensorgrams of sdAb A60401 binding to human transferrin at varying concentrations of sdAb of 2 nM, 1 nM, 0.5 nM, 0.25 nM, and 0.125 nM, from the top to the bottom of the plot; FIG. 4B shows SPR sensorgrams of sdAb A60219 binding to human transferrin at varying concentrations of sdAb A60401 of 2 nM, 1 nM, 0.5 nM, 0.25 nM, and 0.125 nM, from the top to the bottom of the plot;

FIG. 6A shows thermo-denaturation curves of sdAb A602019; FIG. 6B shows thermo-denaturation curves of sdAb A60401; FIG. 6C shows thermo-denaturation curves of sdAb A69433; FIG. 6D shows thermo-denaturation curves of sdAb A69447; and FIG. 6E shows thermo-denaturation curves of sdAb A60449.

DETAILED DESCRIPTION OF THE INVENTION

Figure 1:
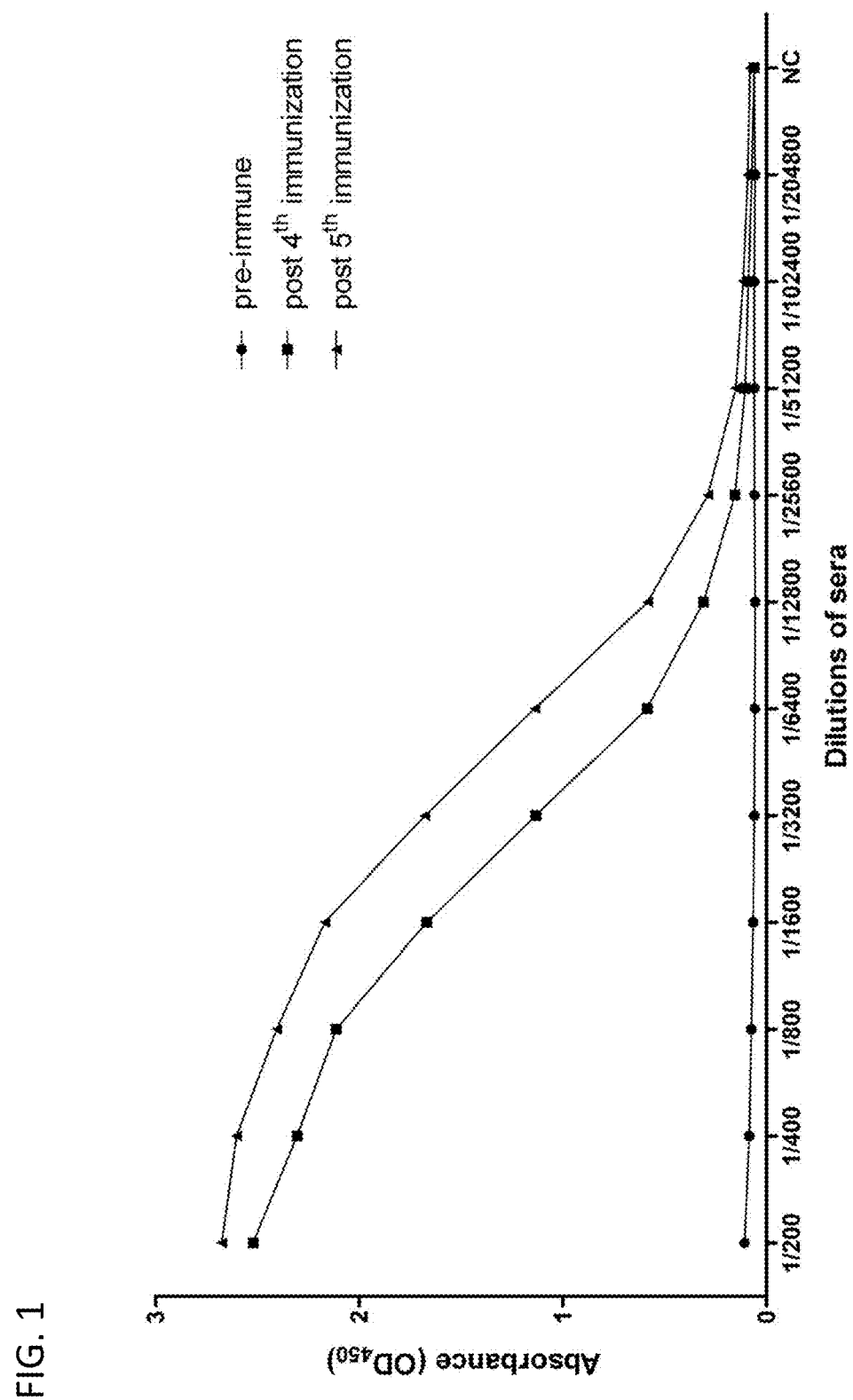
FIG. 1 is a graph showing the immune response of llama against human transferrin after being immunized with an antigen.

Various publications are cited or described in the background and throughout the specification and each of these references is herein incorporated by reference in its entirety. Discussion of documents, acts, materials, devices, articles or the like which has been included in the present specification is for the purpose of providing context for the present invention. Such discussion is not an admission that any or all of the matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. It must be noted that as used herein and in the appended claims, the singular forms "a," "an," and "the" include plural reference unless the context clearly dictates otherwise.

One of ordinary skill in the art will be familiar with the structure of an antibody. The light and heavy chains each contain a variable region that is responsible for binding the target antigen. The variable region contains the antigen binding determinants of the molecule, thus determining the specificity of an antibody for its target antigen. The variable regions of the light and heavy chains comprise three complementarity determining regions (CDRs).

As used herein "complementarity determining region" or "CDR" refers to an amino acid sequence of a variable region of a heavy or light chain of an antibody that contributes to specific recognition of, and binding specificity for, the antigen. The CDRs are referred to as CDR1, CDR2, and CDR3. According to embodiments of the present invention, at least one of the sequences of CDR1, CDR2, and CDR3 contributes to specific recognition of, and binding specificity for, an antibody or fragment thereof against transferrin, and preferably against human transferrin.

An "antibody fragment" as used herein includes any suitable antigen-binding antibody fragment. For example, an antibody fragment can comprise a single-chain variable region. According to embodiments of the present invention, an antibody is preferably a single-domain antibody (sdAb).

As used herein, "single-domain antibody" or "sdAb" refers to the antigen-binding site of a heavy-chain antibody (HCAb) of camelids and sharks, which is naturally devoid of light chains. Camelids include camel, llama, and alpaca. The antigen-binding site of HCAb of camelids is formed by a single variable domain designated VHH. The sdAbs usually exist as monomeric proteins having relatively small sizes. An sdAb according to the invention has three CDRs (CDR1, CDR2, and CDR3).

As used herein, "antibody or fragment thereof against transferrin," "antibody or fragment thereof that specifically binds transferrin," and "transferrin antibody," shall all have the same meaning, and refer to an antibody or fragment thereof, that is capable of binding specifically to transferrin.

As used herein, "sdAb against transferrin," "sdAb that specifically binds transferrin," and "transferrin sdAb," shall all have the same meaning, and refer to a single domain antibody that is capable of binding specifically to transferrin.

As used herein, "transferrin" broadly refers to a protein that binds iron. Transferrin, as used in the present invention, can be a transferrin from any organism that produces transferrin, and is more preferably a mammalian transferrin, such as human transferrin or monkey transferrin, and is most preferably a human transferrin.

As used herein, "binds specifically to" or "against" when used in connection with an antibody or fragment thereof and transferrin refers to the binding or interaction between the antibody and fragment thereof, such as an sdAb, and the transferrin. An antibody or fragment thereof, such as an sdAb, according to the invention binds to a transferrin with a dissociation constant ($K_D$) of between $10^{-6}$ and $10^{-9}$ M, or less, and preferably with a dissociation constant of less than $10^{-9}$ M, e.g., a dissociation constant in the nanomolar to picomolar range ($10^{-9}$ to $10^{-12}$).

Any method known in the art can be used for determining specific antigen-antibody binding including, for example, surface plasmon resonance (SPR), scatchard analysis and/or competitive binding assays, such as radioimmunoassay (RIA), enzyme immunoassays (EIA) and sandwich competition assays, and the different variants thereof known in the art, as well as other techniques mentioned herein. Methods for determining the binding affinities or dissociation constants are known to those skilled in the art.

Any method known in the art can be used for characterizing an antibody or sdAb according to the invention, such as SDS-polyacrylamide gel electrophoresis (PAGE), circular dichroism (CD), size exclusion chromatography (SEC), etc.

Methods for characterizing proteins, i.e. determining the oligomeric state, melting temperature, molecular weight, purity, etc., are known to those skilled in the art.

As used herein, the "half-life" of a protein or polypeptide refers to the time taken for the concentration of the polypeptide to be reduced by 50% in an assay conducted in vivo or in vitro. The reduction can be caused by degradation, clearance, or sequestration of the polypeptide in the assay. The half-life of a polypeptide can be determined by any manner known in the art in view of the present disclosure, such as by pharmacokinetic analysis. For example, to measure the half-life of a protein or polypeptide in vivo, a suitable dose of the polypeptide is administered to a warm-blooded animal (i.e. to a human or to another suitable mammal, such as a mouse, rabbit, rat, pig, dog, or a primate); blood samples or other samples from the animal are collected; the level or concentration of the protein or polypeptide in the sample is determined; and the time until the level or concentration of the polypeptide has been reduced by 50% compared to the initial level upon dosing is calculated based on measured data. See, e.g., Kenneth, A et al., Chemical Half-life of Pharmaceuticals: A Handbook for Pharmacists and Peters et al., Pharmacokinetic analysis: A Practical Approach (1996).

As used herein, "an increase in half-life" or "longer half-life" refers to an increase in any one of the parameters used to describe the protein half-life, such as the $t\frac{1}{2}$-α, $t\frac{1}{2}$β and the area under the curve (AUC), any two of these parameters, or essentially all of these parameters, as compared to a control.

As used herein, a "fusion tag" is a polypeptide sequence that can be operably linked to a target protein or polypeptide to generate a fusion protein for the ease of subsequent manipulation, such as for the expression, purification, in vitro and in vivo analysis and characterization of the protein, or diagnostic or therapeutic application. A fusion tag can exhibit one or more properties. For example, the fusion tag can selectively bind to a purification medium that contains a binding partner for the fusion tag and allows the operably linked target protein or fusion protein to be easily purified. The fusion tag can be, for example, glutathione S-transferase (GST), maltose binding protein, polyhistidine (His-tag), FLAG-tag, avidin, biotin, streptavidin, chitin binding domain, a ligand of a cellular receptor, the Fc region of an antibody, green fluorescent protein, etc.

The present invention relates to antibodies or fragments thereof against transferrin and methods of using antibodies or fragments thereof against a transferrin to increase the half-life of a target protein, i.e., by obtaining a fusion protein comprising a target protein and an antibody or fragment thereof against a transferrin, and exposing the fusion protein to the transferrin, for example, in a serum. The fusion protein can be exposed to the transferrin in a serum either in vitro or in vivo. In a particular embodiment, the invention relates to novel sdAbs against transferrin and their uses.

Accordingly, in one general aspect, the present invention provides an isolated antibody or fragment thereof that specifically binds a transferrin, the antibody or fragment thereof comprising one or more selected from the group consisting of:

(a) a complementarity determining region (CDR) 1 comprising an amino acid sequence selected from the group consisting of GSGFGINGVI (SEQ ID NO: 1); GSGFGVNGVI (SEQ ID NO: 2); GNVFTIAAMG (SEQ ID NO: 3); GNVFTIAAMA (SEQ ID NO: 4); GNVFTIDAMG (SEQ ID NO: 5); GSVFSIDAMG (SEQ ID NO: 6); GNVFGIDAVG (SEQ ID NO: 7); GSIFSIKVMG (SEQ ID NO: 8); and GSIFPLNDMG (SEQ ID NO: 9);

(b) a CDR2 comprising an amino acid sequence selected from the group consisting of LIKSDGYTNYRESVKG (SEQ ID NO: 10); LIKSDGYTNYRESVRG (SEQ ID NO: 11); GITTGGSTNYADSVKG (SEQ ID NO: 12); GMTNGGKTNYADSVKG (SEQ ID NO: 13); AMTNAGSTNYADSVKG (SEQ ID NO: 14); ATTTSGSSTNYADSVKG (SEQ ID NO: 15); DITSGGSTDYSDSVKG (SEQ ID NO: 16); and TITRGGTTNYADSVKG (SEQ ID NO: 17); and (c) a CDR3 having comprising an amino acid sequence selected from the group consisting of PGVP (SEQ ID NO: 18); VTKWAARVGGSAEYE (SEQ ID NO: 19); RSKLIATINNPYDY (SEQ ID NO: 20); RSKLIARINNPYEY (SEQ ID NO: 21); RPKQATLIRDDY (SEQ ID NO: 22); DLGCSGAGSCPDY (SEQ ID NO: 23); and DNRVGGSY (SEQ ID NO: 24).

According to embodiments of the present invention, an isolated antibody, preferably an sdAb, or fragment thereof, comprises a CDR 1 selected from the group consisting of SEQ ID NOs: 1-9, a CDR 2 selected from the group consisting of SEQ ID NOs: 10-17, and a CDR 3 selected from the group consisting of SEQ ID NOs: 18-24.

According to embodiments of the present invention, an isolated antibody or fragment thereof that specifically binds a transferrin has an affinity ($K_D$) for transferrin that is between $10^{-6}$ and $10^{-9}$ M or less, and preferably has an affinity lower than $10^{-9}$ M. In a most preferred embodiment, an isolated antibody or fragment thereof according to the invention has a $K_D$ for transferrin that is in the subnanomolar range, for example, in the picomolar range, such as 1-10 pM, 15 pM, 20 pM, 30 pM, 40 pM, 50 pM, 60 pM, 70 pM, 80 pM, 90 pM, or 100 pM.

In a particular embodiment, an isolated antibody or fragment thereof according to an embodiment of the present invention comprises a CDR1 amino acid sequence of SEQ ID NO: 1, a CDR2 amino acid sequence of SEQ ID NO: 10, and a CDR3 amino acid sequence of SEQ ID NO: 18. In yet another particular embodiment, an isolated antibody or fragment thereof according to the present invention comprises a CDR1 amino acid sequence of SEQ ID NO: 3, a CDR2 amino acid sequence of SEQ ID NO: 12, and a CDR3 amino acid sequence of SEQ ID NO: 19. In other particular embodiments, an isolated antibody or fragment thereof according to the present invention comprises a CDR1 amino acid sequence of SEQ ID NO: 6, a CDR2 amino acid sequence of SEQ ID NO: 14, and a CDR3 amino acid sequence of SEQ ID NO: 21; a CDR1 amino acid sequence of SEQ ID NO: 7, a CDR2 amino acid sequence of SEQ ID NO: 15, and a CDR3 amino acid sequence of SEQ ID NO: 22; or a CDR1 amino acid sequence of SEQ ID NO: 9, a CDR2 amino acid sequence of SEQ ID NO: 17, and a CDR3 amino acid sequence of SEQ ID NO: 24.

According to embodiments of the present invention, an antibody or fragment thereof, such as an sdAb, that specifically binds a transferrin can comprise an amino acid sequence selected from the group consisting of SEQ ID NOs: 26, 28, 30, 32, 34, 36, 38, 40, 42, 44, 46, 48, 50, 52, 54, 56, 58, 60, and 62.

According to a preferred embodiment of the present invention, an antibody or fragment thereof that specifically binds transferrin is an sdAb. For example, an sdAb according to the invention that specifically binds transferrin can be a camelid $V_HH$ antibody.

In a particularly preferred embodiment of the present invention, an sdAb that specifically binds transferrin comprises the amino acid sequence of A60219:
(SEQ ID NO: 26)
QVQLVESGGGLVQAGGSLRLSCVASGSGFGINGVIWYRQAPGKQRELVAL

IKSDGYTNYRESVKGRFTISRDDAKNTVWLQMNALEPEDTGVYYCKTPGV

PFGQGTQVTVSS;

the amino acid sequence of A60401:
(SEQ ID NO: 28)
QVKLEESGGGLVQAGGSLRLSCEASGNVFTIAAMGWFRQAPGKERELVAG

ITTGGSTNYADSVKGRFTISRDNAQNTMYLQMNSLRPEDTAAYSCNAVTK

WAARVGGSAEYEYWGQGTQVTVSS;

the amino acid sequence of A69449:
(SEQ ID NO: 56)
QVQLVESGGGVVQAGGSLRLSCVASGSVFSIDAMGWYRQAPGNQRELVAA

MTNAGSTNYADSVKGRFTISRDNAENTVYLQMNSLKPEDTAVYYCNARSK

LIARINNPYEYWGQGTQVTVSS;

the amino acid sequence of A69433:
(SEQ ID NO: 58)
QVKLEESGGGLVQAGGSLRLSCVASGNVFGIDAVGWYRQAPGKQRELVAA

TTTSGSSTNYADSVKGRFTISRDIAKNTVYLQMDSLKPEDTAVYYCYARP

KQATLIRDDYWGQGTQVTVSS;
or the amino acid sequence of A69447:
(SEQ ID NO: 62)
QVKLEESGGGSVQAGGSLRLSCTGSGSIFPLNDMGWYRQAPGKQRELVAT

ITRGGTTNYADSVKGRFTISRDSNAKNTVYLQMNSLKVEDTAVYYCNMDN

RVGGSYWGQGTQVTVSS.

The present invention also provides a nucleic acid comprising a complementary DNA (cDNA) sequence encoding an antibody or fragment thereof according to an embodiment of the invention. Also provided are vectors comprising the nucleic acid molecule, particularly expression vectors, and recombinant host cells comprising the vectors that can subsequently be used for downstream applications such as expression, purification, etc. The nucleic acid molecules, vectors and host cells can be obtained using methods known in the art in view of the present disclosure.

An antibody or fragment thereof according to embodiments of the invention can be produced recombinantly from a recombinant host cell using methods known in the art in view of the present disclosure. The recombinantly produced antibody or fragment thereof can be different from the naturally occurring antibody or fragment thereof, for example, in posttranslational modification of amino acids. As used herein, "posttranslational modification of amino acids" refers to any modification to the amino acids after translation of the amino acids, such as by attaching to one or more amino acids independently one or more biochemical functional groups (such as acetate, phosphate, various lipids and carbohydrates), changing the chemical nature of an amino acid (e.g. citrullination), or making structural changes (e.g. formation of disulfide bridges).

According to embodiments of the present invention, a nucleic acid molecule comprises a cDNA or synthetic DNA sequence encoding an amino acid sequence selected from the group consisting of SEQ ID NOs: 26, 28, 30, 32, 34, 36, 38, 40, 42, 44, 46, 48, 50, 52, 54, 56, 58, 60, and 62. In particular embodiments of the present invention, the nucleic acid molecule comprises a cDNA or synthetic DNA sequence comprising a sequence selected from the group consisting of SEQ ID NOs: 25, 27, 29, 31, 33, 35, 37, 39, 41, 43, 45, 47, 49, 51, 53, 55, 57, 59 and 61. However, one skilled in the art will recognize that the specific nucleotide sequences listed are intended to be non-limiting examples, and various nucleotide sequences can encode the same amino acid sequence.

As used herein, a "cDNA or synthetic DNA" refers to a DNA molecule that is different from a naturally occurring DNA molecule in at least one of the nucleotide sequence and the physical or chemical property of the DNA molecule. For example, the "cDNA or synthetic DNA" can be different from the naturally occurring DNA in nucleotide sequence by not containing one or more introns present in the natural genomic DNA sequence. The "cDNA or synthetic DNA" can also be different from a naturally occurring DNA in one or more physical or chemical properties, such as having a different DNA modification, regardless of whether the "cDNA or synthetic DNA" comprises the same or different nucleotide sequence as that of the naturally occurring DNA.

As used herein, "DNA modification" refers to any modification to the DNA, such as by independently attaching to one or more nucleotides of the DNA one or more biochemical functional groups (such as a methyl group, phosphate group, etc). Different host cells can have different DNA modification systems, thus producing different DNA molecules even though the DNA molecules can have identical nucleotide sequence.

A "cDNA or synthetic DNA" can be made by any method in vivo or in vitro so long as the obtained "cDNA or synthetic DNA" is distinguishable from a naturally occurring DNA molecule. For example, a "cDNA" can be made from a messenger RNA (mRNA) template in a reaction catalyzed by the enzymes reverse transcriptase and DNA polymerase, or RNA-dependent DNA polymerase. In one embodiment, a "cDNA" can be made and amplified via a reverse transcriptase polymerase chain reaction (RT-PCR) with the desired mRNA template and DNA primers. A "synthetic DNA" can be made in vitro using any method known in the art. A "synthetic DNA" can also be made in vivo in a host cell that does not naturally contain a nucleic acid molecule having the identical nucleotide sequence as that of the "synthetic DNA," such that the "synthetic DNA" made by the host cell is distinguishable from any naturally occurring DNA sequence in at least one or more physical or chemical properties, such as DNA methylation.

Embodiments of the present invention also relate to methods of recombinantly expressing and purifying an antibody or fragment thereof that specifically binds transferrin. According to embodiments of the present invention, the method comprises obtaining an expression vector encoding an antibody or fragment thereof according to an embodiment of the invention, introducing the expression vector into a host cell to obtain a recombinant cell, growing the recombinant cell under conditions that allow expression of the antibody or fragment thereof, and obtaining the antibody or fragment thereof from the recombinant cell. The antibody or fragment thereof that specifically binds transferrin can be isolated by applying the lysate, supernatant, or periplasmic extract of the recombinant cell comprising the antibody or fragment thereof, to an affinity column associated with the transferrin.

In another embodiment, the antibody or fragment thereof that specifically binds a transferrin further comprises a fusion tag that facilitates purification of the antibody or fragment thereof from the recombinant cell, by for example, applying the lysate, supernatant, or periplasmic extract of the recombinant cell comprising of the antibody or fragment thereof, to an affinity column associated with a binding partner of the fusion tag. As an illustrative and non-limiting example, a fusion tag can be a 6×-HIS tag, and the 6×-HIS tagged antibody or fragment thereof can be purified from the recombinant cell by applying the lysate, supernatant, or periplasmic extract of the recombinant cell to a nickel column.

Antibodies or fragments thereof, and particularly sdAbs, according to embodiments of the invention that specifically bind transferrin have high affinity for transferrin (e.g., picomolar range) and a longer half-life in a serum supplemented with transferrin, as compared to the half-life in a serum that is not supplemented with the transferrin. Without wishing to be bound by theory, it is believed that the binding interaction between the antibody and fragment thereof, such as sdAb, and the transferrin contributes to the longer half-life of the antibody or fragment thereof in a serum. Such antibody or fragment thereof can thus be used to increase the half-life of a target protein fused to the antibody or fragment thereof in a serum, or in a composition comprising the transferrin.

Thus, in another general aspect, the present invention relates to a method of increasing the half-life of a target protein in a serum. The method comprises (1) obtaining a fusion protein, wherein the fusion protein comprises an antibody or fragment thereof that specifically binds a transferrin, the target protein, and optionally a linker, wherein the antibody or fragment thereof is fused to the carboxyl-terminus or amino-terminus of the target protein, and the linker optionally separates the antibody and the carboxyl-terminus or amino-terminus of the target protein; and (2) exposing the fusion protein to the transferrin to thereby increase the half-life of the target protein in the fusion protein compared to the target protein alone.

According to embodiments of the present invention, the transferrin used in the exposing step can be present in any composition, including a serum or a buffered composition made in vitro. Preferably, the fusion protein is exposed to the transferrin by administering it to a serum comprising the transferrin.

According to embodiments of the present invention, when exposed to the transferrin, the fusion protein has an increased half-life, as determined, for example by measuring the half-life, as compared to the target protein alone. The fusion protein can optionally contain a linker that fuses the target protein to the antibody or fragment thereof, and also functions to separate the target protein from the antibody or fragment thereof. Linkers that can be used to fuse two protein molecules together will be well known to those skilled in the art in view of the present disclosure.

The antibody or fragment thereof can be fused to the target protein by any method known in the art in view of the present disclosure, such as, for example, via genetic fusion or covalent linkage. The antibody or fragment thereof can be fused to either the amino-terminus or the carboxyl-terminus of the target protein.

Preferably, the fusion protein comprises an antibody or fragment thereof according to embodiments of the present invention. For example, the antibody or fragment thereof comprises an amino acid sequence selected from the group consisting of the amino acid sequence of CDR1 comprising the sequence of SEQ ID NO: 1, 2, 3, 4, 5, 6, 7, 8, or 9; the amino acid sequence of CDR2 comprising the sequence of SEQ ID NO: 10, 11, 12, 13, 14, 15, 16, or 17; and the amino acid sequence of CDR3 comprising the sequence of SEQ ID NO: 18, 19, 20, 21, 22, 23, or 24. Most preferably, the antibody or fragment thereof of the fusion protein is an sdAb and even more preferably is an sdAb comprising the amino acid sequence of A60219 (SEQ ID NO: 26), A60401 (SEQ ID NO: 28), A69449 (SEQ ID NO: 56), A69433 (SEQ ID NO: 58), or A69447 (SEQ ID NO: 62).

According to embodiments of the present invention, the target protein is a peptide or polypeptide, such as a therapeutic polypeptide, a polypeptide that can be used for a diagnostic purpose, or a polypeptide for structural-activity studies. For example, the target protein can be an antibody, peptide, or any other polypeptide that has been or will be developed or used for a therapeutic or diagnostic purpose, or a protein subjected to structural and/or functional analysis. Preferably, the target protein is a therapeutic peptide or polypeptide that is unstable in serum, and in need of increased serum half-life to be used for therapeutic, diagnostic purposes, etc.

The fusion proteins according to embodiments of the present invention can be used for various purposes using methods known in the art in view of the present disclosure. For example, a fusion protein can be used for assaying the affinity of the target protein to a binding partner, e.g., for drug screening or target identification purposes. It can also be used in a diagnostic method, particularly if the method involves administering the target protein to the serum. It can further be used for therapeutic purposes, particularly if the target protein is known to be unstable in serum.

Another general aspect of the invention relates to a composition comprising an effective amount of a fusion protein, wherein the fusion protein comprises an antibody or fragment thereof that specifically binds a transferrin, a target protein, and optionally a linker, wherein the antibody or fragment thereof is fused to the carboxyl-terminus or amino-terminus of the target protein, and the linker optionally separates the antibody and the carboxyl-terminus or amino-terminus of the target protein. Preferably, the composition further comprises the transferrin, which increases the half-life of the fusion protein in the composition. The composition can further comprise a pharmaceutically acceptable carrier, which can comprise any carrier that is suitable for pharmaceutical or diagnostic purposes.

Depending on the use, the effective amount can be the amount of the fusion protein that is effective to provide a therapeutic or diagnostic use of the target protein as part of the fusion. For example, an effective amount of the fusion protein, when used for a therapeutic application, can be the amount fusion protein that treats and/or prevents a disease, disorder, or condition treatable or preventable by the target protein as part of the fusion protein. An effective amount of the fusion protein, when used for a diagnostic application, can be the amount of the fusion protein needed to detect a marker, e.g., biomolecule such as nucleic acid or protein, by the target protein as part of the fusion protein.

A composition according to an embodiment of the present invention can be used in vivo or in vitro for any purpose. Compositions of the invention for in vivo uses can be formulated for any method of delivery to a subject, e.g., a mammal, such as human, rat, mice, monkey, or rabbit, including, but not limited to oral, topical, and injection. Preferably a composition for in vivo use is formulated for injection or intravenous administration.

The present invention also relates to a method comprising exposing a composition according to an embodiment of the present invention to the transferrin to thereby increase the half-life of the target protein in the fusion protein.

In one embodiment, the present invention relates to a method comprising exposing a composition according to an embodiment of the present invention to the transferrin used in the fusion protein, for example, by administering the composition to a serum comprising transferrin, in vivo or in vitro for identifying a diagnostic or therapeutic agent.

In another embodiment, a method according to the present invention comprises administering a composition according to an embodiment of the present invention to a subject in need of treatment by the target protein, wherein the composition comprises a therapeutically effective amount of a fusion protein comprising an antibody or fragment thereof that specifically binds the human transferrin and a target protein.

In yet another embodiment, a method according to the invention comprises administering the composition to a subject in need of a diagnosis by the target protein, wherein the composition comprises a diagnostically effective amount of the fusion protein.

Embodiments of the present invention also relate to compositions comprising a fusion protein according to the invention, and methods for increasing the half-life of a target protein in a composition. A method for increasing the half-life of a target protein in a composition comprises obtaining a fusion protein, preferably isolated fusion protein, comprising an antibody or fragment thereof against a transferrin, the target protein and an optional linker, wherein the antibody or fragment thereof is fused to the carboxyl-terminus or amino-terminus of the target polypeptide, and the optional linker separates the antibody or fragment thereof and the carboxyl-terminus or amino-terminus of the target polypeptide; and exposing the fusion protein to the transferrin in the composition, wherein the fusion protein has a longer half-life than the target protein alone in the composition.

Without wishing to be bound by theory, it is believed that the specific binding between the antibody or fragment thereof in the fusion protein and the transferrin in a composition or a serum contributes to increased half-life of the target protein.

Embodiments of the present invention also provides methods for obtaining a target protein having increased serum half-life, and for expressing and purifying a fusion protein comprising an antibody or fragment thereof that binds to a transferrin and a target protein.

According to embodiments of the present invention, a method for obtaining a target protein having increased serum half-life comprises:

(a) obtaining an expression vector encoding a fusion protein comprising an antibody or fragment thereof that specifically binds a transferrin, the target protein, and an optional linker, wherein the antibody or fragment thereof is fused to the carboxyl-terminus or amino-terminus of the target protein, and the optional linker separates the antibody and the carboxyl-terminus or amino-terminus of the target protein;

(b) introducing the expression vector of step (a) into a cell to obtain a recombinant cell;

(c) growing the recombinant cell under conditions to allow expression of the fusion protein; and (d) obtaining the fusion protein from the recombinant cell.

Expression vectors encoding the fusion protein and recombinant cells expressing the fusion protein can be constructed using methods known in the art in view of the present disclosure. Any host cell suitable for recombinant production of the fusion protein can be used such as a mammalian cell, plant cell, yeast cell, or bacterial cell. Preferably, the host cell is a bacterial cell, and is more preferably *Escherichia coli*. Any method for obtaining the fusion protein from the recombinant cell can be used in view of the present disclosure including, but not limited to, column chromatography such as affinity chromatography.

In one embodiment, the fusion protein can be obtained from a recombinant cell and purified by utilizing the specific interaction between the portion of the fusion protein comprising the antibody or fragment thereof that specifically binds transferrin, and transferrin, to obtain the fusion protein from the recombinant cell, e.g., by affinity chromatography using an affinity column associated with transferrin.

In another embodiment, the fusion protein can further comprise a fusion tag at the amino-terminus or carboxyl-terminus of the fusion protein to facilitate obtaining and purifying the fusion protein from the recombinant cell. The fusion tag can be fused to the transferrin, or to the antibody or fragment thereof that binds transferrin. For example, the lysate, periplasmic extract, or supernatant of the recombinant cell comprising the fusion protein can be obtained and applied to a column associated with the appropriate binding partner of the fusion tag. In a particular and non-limiting example, the fusion protein can further comprise a His-tag and the lysate, periplasmic extract, or supernatant of the recombinant cell comprising the fusion protein can be obtained and applied to a nickel column to obtain the fusion protein from the recombinant cell. The column can then be washed, and the fusion protein eluted from the column under the appropriate buffering conditions to obtain the fusion protein.

Another general aspect of the present invention relates to a system for increasing the half-life of a target protein, comprising:

(1) an expression vector comprising a first nucleotide sequence encoding an antibody or fragment thereof that specifically binds a transferrin, and optionally a second nucleotide sequence encoding a linker, wherein the first and second nucleotide sequences are operably linked;

(2) a host cell; and (3) the transferrin.

The expression vector can be used to construct an expression vector for a fusion protein comprising an antibody or fragment thereof that specifically binds a transferrin, a target protein, and optionally a linker, wherein the antibody or fragment thereof is fused to the carboxyl-terminus or amino-terminus of the target protein, and the linker optionally separates the antibody and the carboxyl-terminus or amino-terminus of the target protein. Thus, in certain embodiments of the invention, an expression vector comprises a first nucleotide sequence encoding an antibody or fragment thereof that specifically binds a transferrin, optionally a second nucleotide sequence encoding a linker, and a third nucleotide sequence encoding a target protein, wherein the first, second, and third nucleotide sequences are operably linked, such that the antibody or fragment thereof is fused to the carboxyl-terminus or amino-terminus of the target protein, and the linker optionally separates the antibody and the carboxyl-terminus or amino-terminus of the target protein.

The host cell can be used to construct a recombinant cell for expressing the fusion protein, e.g., by transforming the host cell with the expression vector for the fusion protein, using any method known in the art in view of the present invention, including but not limited to electroporation and calcium chloride transformation.

The transferrin can be used to stabilize the fusion protein. It can also be used to isolate the fusion protein by affinity chromatography.

According to an embodiment of the present invention, the system can further comprise a solid support for capturing the fusion protein via specific binding between the antibody or fragment thereof in the fusion protein and the transferrin associated with the solid support, or via specific binding between a fusion tag on the fusion protein and a binding partner of the fusion tag associated with the solid support.

The system can further comprise one or more buffers useful for the expression and/or isolation of the fusion protein.

The following specific examples of the invention are further illustrative of the nature of the invention, and it needs to be understood that the invention is not limited thereto.

EXAMPLES

Example 1: Production and Characterization of sdAbs that Specifically Bind a Transferrin Materials and Methods Isolation of Transferrin sdAbs from a Llama Immune Phage Display Library A male llama (*Lama glama*) was injected subcutaneously with 100 µg, 50 µg, 50 µg, 10 µg, and 10 µg human transferrin on days 1, 22, 36, 50 and 64, respectively [11]. Complete Freund's Adjuvant (Sigma, St. Louis, Mo.) was used for the primary immunization and Incomplete Freund's Adjuvant was used for subsequent immunizations 2-4. Adjuvant was not used for the final immunization. The llama was bled one week following each immunization and heparinized blood was collected for immediate isolation of the peripheral blood leukocytes, which were then stored at −80° C. until further use.

Total RNA was isolated from $1 \times 10^8$ leukocytes using a QIAamp RNA Blood Mini Kit (Qiagen). cDNA was synthesized using pd(N)$_6$ as primer and 566 ng total RNA as the template. Four forward primers P441_VHHF1 (GCCCAGCCGGCCATGGCCSMBGTRCAGCTGGTG-GAKTCTGGGGGA; SEQ ID NO: 63), P442_VHHF2 (GCCCAGCCGGCCATGGCCCAGGTAAAGCTGGAG-GAGTCTGGGGGA; SEQ ID NO: 64), P759_VHHF3 (GCCCAGCCGGCCATGGCCCAGGTACAGCTGGTG-GAGTCT; SEQ ID NO: 65) and P444_VHHF4 (GCCCAGCCGGCCATGGCCGAGGTGCAGCTGGTG-GAGTGTGG; SEQ ID NO: 66); and two reverse primers P445_CH2R (CGCCATCAAGGTACCAGTTGA; SEQ ID NO: 67) and P446_CH2b3R (GGGGTACCTGTCATC-CACGGACCAGCTGA SEQ ID NO: 68) were used to amplify $V_H$-$C_H$1-Hinge-$C_H$2 region of conventional immunoglobulin G antibody (IgG) or $V_H$H-Hinge-$C_H$2 of heavy chain antibody. Amplified $V_H$H products of approximately 600 bp from the primer combinations of P445_$C_H$2R with each of the forward primers P441_VHHF1, P442_VHHF2, P759_VHHF3, and P444_VHHF4 were extracted from a 1% agarose gel, and purified with a QIAquick Gel Extraction Kit (Qiagen) and the amplified products from primers P446_$C_H$2R were PCR purified. In a second PCR reaction, two primers, P440_VHHF (CATGTGTA-GACTCGCGGCCCAGCCGGCCATGGCC; SEQ ID NO: 69) and P447_VHHR (CATGTGTAGAT-TCCTGGCCGGCCTGGCCTGAGGA-GACGGTGACCTG; SEQ ID NO: 70) were used to introduce SfiI restriction sites, and to amplify the final sdAb fragments from the combined amplified products. The final PCR product was digested with SfiI and ligated into a conventional phagemid vector constructed at GenScript Inc., and transformed into *E. coli* TG1 by electroporation. Phage were rescued and amplified with helper phage M13KO7 (New England Biolabs (NEB)).

The llama immune phage display library was panned against transferrin that was conjugated to M-280 beads (Invitrogen). Approximately $3 \times 10^{11}$ phages were added to the beads and incubated at 37° C. for 2 hours for antigen binding. After disposal of unbound phages, the beads were washed six times with phosphate buffered saline supplemented with 0.05% Tween 20 (PB ST) for round one, and the washes were increased by one for each additional round. Phages were eluted by 10 min incubation with 100 µl 100 mM triethylamine, and the eluate was subsequently neutralized with 200 µl M Tris-HCl (pH 7.5). Phages were amplified as described above, but on a smaller scale. After two rounds of panning, eluted phages were used to infect exponentially growing *E. coli* TG1. Individual colonies were used in phage enzyme-linked immunosorbent assay (ELISA).

For phage ELISA, a 96-well microliter plate was coated overnight with 2 µg/ml human transferrin and then blocked with 4% modified phosphate buffered saline (MPBS) for 2 hours at 37° C. Phage from individual clones were pre-blocked with 4% MPBS overnight, added to the pre-blocked wells and incubated for 1 hour. Phage ELISA was performed using the GE Healthcare Detection Module Recombinant Phage Antibody System (GE Healthcare, Uppsala, Sweden) and positive phage clones were sequenced.

Expression of sdAbs

DNA encoding each sdAb (A60401, A60219, A69433, A69447, or A69449) (FIG. 2) was cloned into the BbsI and BamHI sites of a periplasmic expression vector pSJF2H [12], which added a 5× Histidine purification tag at the C-terminus of the sdAbs. These sdAbs were expressed periplasmically and purified by immobilized metal ion affinity chromatography (IMAC) [13]. Briefly, clones were inoculated in 25 ml LB-Ampicillin (Amp) and incubated at 37° C. with 200 rpm shaking overnight. The next day, 20 ml of the culture were used to inoculate 1 L of M9 medium (0.2% glucose, 0.6% Na$_2$HPO$_4$, 0.3% KH$_2$PO$_4$, 0.1% NH$_4$Cl, 0.05% NaCl, 1 mM MgCl$_2$, 0.1 mM CaCl$_2$)) supplemented with 0.4% casamino acids, 5 mg/L of vitamin B1, and 200 µg/ml of Amp, and cultured for 24 hours. 100 ml of 10×TB nutrients (12% Tryptone, 24% yeast extract and 4% glycerol), 2 ml of 100 mg/ml Amp, and 1 ml of 1 M isopropyl-beta-D-Thiogalactopyranoside (IPTG) were added to the culture and incubation was continued for another 65-70 hours at 28° C. with 200 rpm shaking. *E. coli* cells were harvested by centrifugation and lysed with lysozyme. Cell lysates were centrifuged, and clear supernatant was loaded onto High-Trap™ chelating affinity columns (GE Healthcare), and His-tagged proteins were purified.

Surface Plasmon Resonance (SPR) Analysis

Experiments were performed using a BIAcore T200 optical sensor platform and research grade CM5 sensor chips (GE Healthcare). Human transferrin was immobilized on the sensor chip surface by standard amine coupling. All experiments were carried out in HEPES buffer [10 mM HEPES (pH 7.4), 150 mM NaCl, 3.4 mM EDTA, 0.005% Tween 20] at 25° C. Antibodies were injected at serial dilutions ranging from 0.25 nM to 16 nM at a flow rate of 30 µl/min unless otherwise indicated. The amount of bound analyte after subtraction from the blank control surface is shown as relative response units (RU). The double referenced sensorgrams from each injection series were analyzed for binding kinetics using BIA evaluation software (GE Healthcare). Dissociation constants ($K_D$s) were calculated from the onand off-rates ($k_{on}$ and $k_{off}$, respectively), as determined by global fitting of the experimental data to a 1:1 Langmuir binding model (Chi$^2$<1).

Size Exclusion Chromatography

Size exclusion chromatography (SEC) analyses of sdAbs, A60401 and A60219, (FIG. 5) were performed with a Superdex 200™ column (GE Healthcare). Superdex separations were carried out in PBS. Low molecular weight (MW) markers ribonuclease A (13.7 kDa), chymotrypsin A (25 kDa) and ovalbumin (43 kDa) were used to calculate the MW of the sdAbs.

Measurement of Melting Temperature of sdAbs by Circular Dichroism

Proteins were separated with a Superdex75 SEC column in 10 mM phosphate buffer, pH 7.0. Peaks representing major components of proteins were collected and used in circular dichroism (CD) analysis. CD spectra were collected from 250 to 200 nm at protein concentrations of 100 ug/ml in a 10 mm quartz cuvette with a J-815 CD spectrometer (JASCO). CD spectra were measured at 2° C. intervals from 30° C. to 90° C. to determine thermal denaturation of proteins with a temperature shift speed of 1° C./min. Ellipticity at 202 nm, 208 nm, and 217 nm was plotted against temperature, and melting temperatures ($T_m$s) were calculated as the average $T_m$ at the three wavelengths.

Measurement of Serum Half-Life

A group of three female Wister rats, each weighing approximately 250 g, were intravenously (i.v.) injected with 30 mg human transferrin, and 500 μg sdAb A60219, A60401, A69433, A69447, or A69449, respectively, immediately after injecting 30 mg human transferrin into the tail vein. Blood was collected from the eye through a glass capillary at indicated time points. Sera were separated and stored at −80° C. until further use. Concentrations of the injected antibody molecules in the above collected samples were measured by ELISA.

For the detection of transferrin, anti-transferrin antibody [HTF-14] (Abcam, ab769) was coated on microtitre plates (Costar, 9018) overnight at 4° C. at a concentration of 1 μg/ml. After washing three times with PBST, plates were blocked with 1% BSA in PBST for two hours at 37° C. Diluted sera (1% BSA in 0.05% PBS-T used as diluent) were added to the wells and incubated at 37° C. for 2 hours. After washing four times with PBST, HRP labeled anti-transferrin antibody (0.1 μg/ml) (Abcam, ab9538) was added to the wells and incubated for another 1 hour. After washing the plate with PBST, the color was developed with TMB substrate for 10 minutes, and the reaction was stopped by adding 1 M HCl. The absorbance of each well was measured at 450 nm using a spectrometer. Serial dilutions of pure human transferrin in 1% BSA in PBST were used to generate a standard curve for human transferrin concentration analysis.

The same method was used for the detection of sdAbs, except anti-sdAb rabbit polyclonal antibody (GenScript) was used as a capture antibody, and HRP labeled anti-sdAb rabbit polyclonal antibody (0.1 μg/ml) (GenScript) was used as detection antibody. Serial dilutions of pure sdAbs in 1% BSA in PBST were used to make a standard curve for the concentration of the sdAbs.

Results

Isolation and Characterization of sdAbs

Isolation of transferrin-specific sdAbs was achieved by llama immunization with human transferrin, construction of an immune phage display library from the llama, and subsequent panning.

Human transferrin induced a medium immune response in the llama. An approximately 25,000 fold dilution of the serum after the fifth immunization still detected positive (FIG. 1). This level of response is in agreement with what is usually achieved with llama immunization.

Approximately 1×10$^8$ llama leukocytes were used for the isolation of mRNA, which was then used for the construction of a phage library. The size of the obtained library was 2×10$^8$ independent transformants with a positive insertion rate of 92%. Two rounds of phage display panning were performed on immobilized transferrin, and phage enrichment was observed during panning (data not shown). Phage ELISA showed that approximately 88% of the analyzed clones bound to transferrin. Analysis of encoding sequences of the sdAbs displayed on the phage clones revealed 19 different sdAb amino acid sequences (SEQ ID NOs: 26, 28, 30, 32, 34, 36, 38, 40, 42, 44, 46, 48, 50, 52, 54, 56, 58, 60 and 62, and FIG. 2).

Figure 3B:
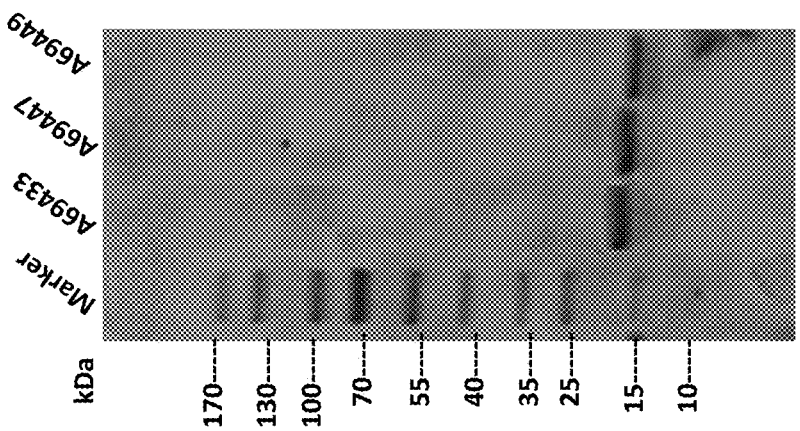
FIGS. 3A and 3B are images of an SDS polyacrylamide gel of purified sdAbs A60219, A60401, A69433, A69447, and A69449, isolated from *Escherichia coli*, the amino acid sequences of which are shown in FIG. 2.
Figure 3A:
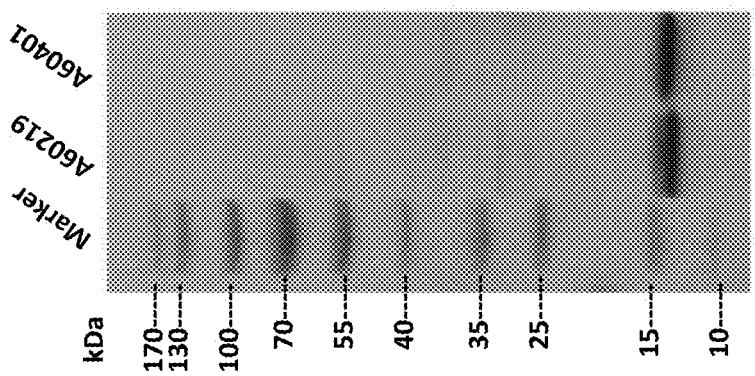

Five sdAbs, A60219, A60401, A69433, A69447 and A69449, were sub-cloned, respectively, into an *E. coli* periplasmic expression vector, pSJF2H [12]. The sdAbs, tagged with a 6× histidine (His) tag at their C-terminal ends, were then produced in *E. coli* and purified by IMAC (FIGS. 3A and 3B). The sdAb yields of A60219, A60401, A69433, A69447 and A69449 were 8.4, 8.5, 12.5, 17.2, and 7.8 mg per liter of TG1 culture, respectively.

The five transferrin sdAbs, A60219, A60401, A69433, A69447 and A69449, were analyzed for binding to transferrin using an SPR-based biosensor (FIG. 4). Among them, A69433, A69447 and A69449, showed excellent cross binding activities with human and monkey transferrins (Table 2).

Figure 4B:
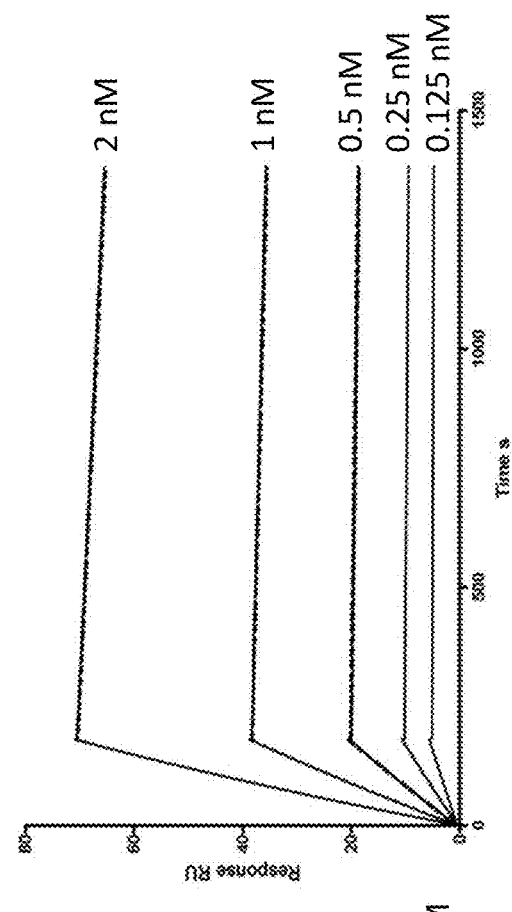
FIGS. 4A and 4B show surface plasmon resonance (SPR) sensorgrams of transferrin sdAbs binding to human transferrin.
Figure 4A:
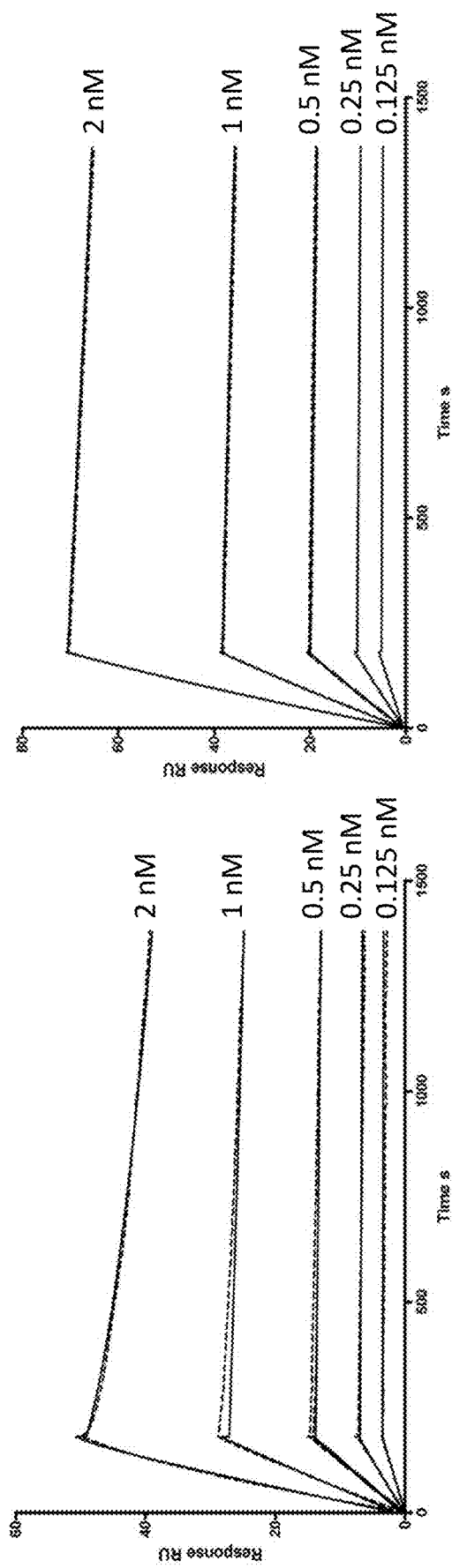

The results are shown in Table 1 and Table 2 below, and in FIG. 4. For example, the on-rates of the sdAbs were 9.27×10$^5$ and 5.14×10$^7$ M$^{-1}$s$^{-1}$, and the off-rates 6.22×10$^{-5}$ and 6.74×10$^{-4}$ s$^{-1}$ for A60401 and A60219, respectively. The dissociation constants ($K_D$s) of the sdAbs were calculated as 67.14 pM for A60401 (FIG. 4A) and 13.1 pM for A60219 (FIG. 4B).

TABLE 1

Transferrin sdAbs (A60219 and A60401) binding to human transferrin measured using SPR.

| Antibody ID | Antigen | $k_{on}$ (1/Ms) | $k_{off}$ (1/s) | $K_D$ (M) |
| --- | --- | --- | --- | --- |
| A60219 | Human transferrin | 5.14E+07 | 6.74E−04 | 1.31E−11 |
| A60401 | Human transferrin | 9.27E+05 | 6.22E−05 | 6.71E−11 |

TABLE 2

Transferrin sdAbs (A69433, A69447 and A69449) binding to human and monkey transferrins measured using SPR.

| Antibody ID | Antigen | $k_{on}$ (1/Ms) | $k_{off}$ (1/s) | $K_D$ (M) |
| --- | --- | --- | --- | --- |
| A69433 | Human Transferrin | 1.11E+05 | 6.42E−04 | 5.76E−09 |
| A69447 |  | 2.03E+05 | 2.09E−04 | 1.03E−09 |
| A69449 |  | 3.42E+05 | 6.95E−04 | 2.03E−09 |
| A69433 | Monkey Transferrin | 2.47E+05 | 5.93E−04 | 2.40E−09 |
| A69447 |  | 3.04E+05 | 7.58E−05 | 2.50E−10 |
| A69449 |  | 4.71E+05 | 5.29E−04 | 1.12E−09 |

Characterization of the sdAbs

Figure 5:
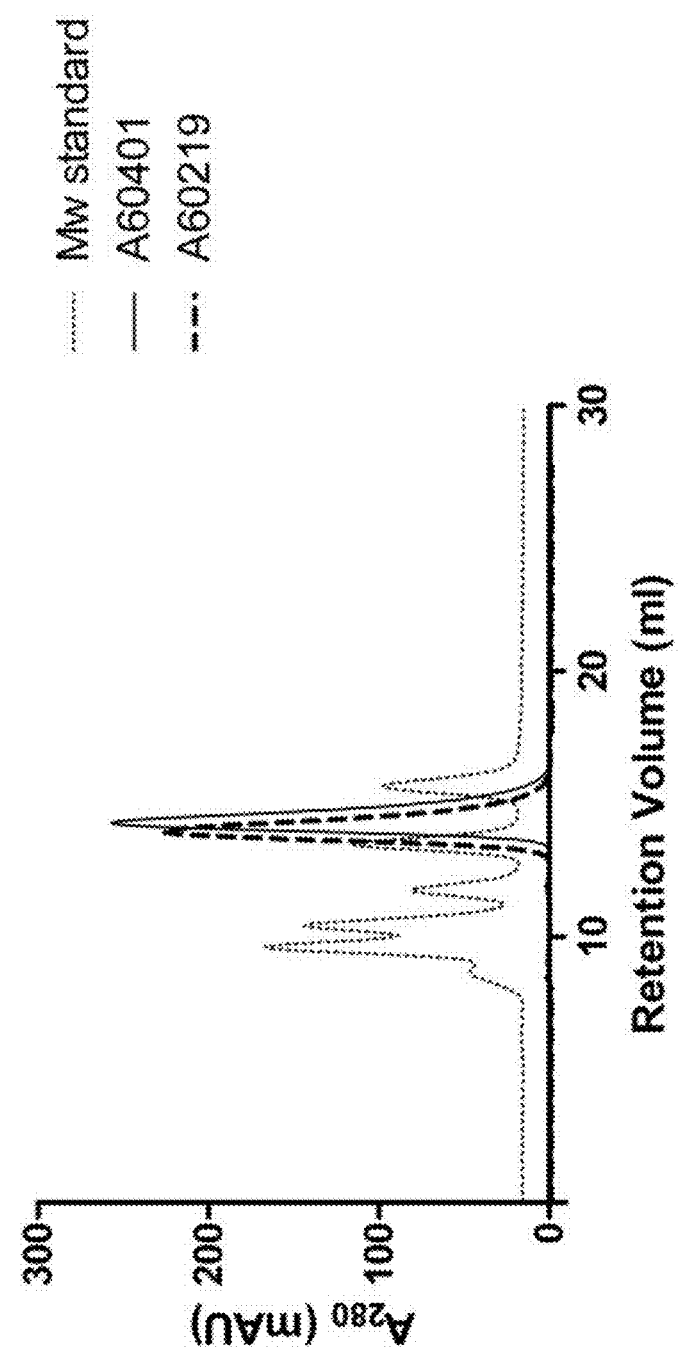
FIG. 5 is a chromatogram of size exclusion chromatography (SEC) analysis of transferrin sdAbs A60401 and A60219.

Size exclusion chromatography (SEC) was employed to evaluate whether the two sdAbs A60401 and A60219 existed as monomers (FIG. 5). As with most camelid sdAbs, A60401 was a pure monomer, which was demonstrated as a single peak at 14.28 ml of elution volume through size exclusion chromatography with a Superdex75 column, corresponding to a measured MW of 10.6 kDa, very close to its calculated MW of 14,347 Da. A60219 very likely exists as pure monomer as well, as it has a single elution peak at 13.98 ml, representing an estimated MW of 11.2 kDa. However, its slightly faster elution from the column than A60401 indicates that dynamic transfer between monomeric and oligomeric forms of A60219 may exist, as it eluted faster than A60401 even with a smaller calculated MW (13,170 Da).

Figure 6A:
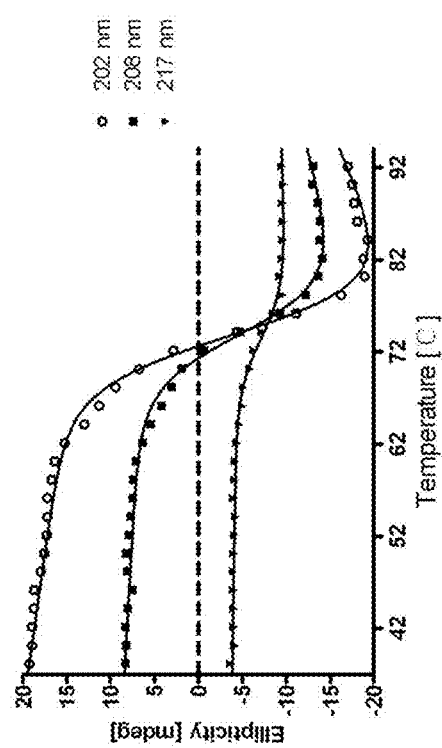
FIGS. 6A, 6B, 6C, 6D, and 6E show graphs of thermo-denaturation curves of transferrin sdAbs measured by circular dichroism (CD) at 202 nm, 208 nm, and 217 nm.
Figure 6B:
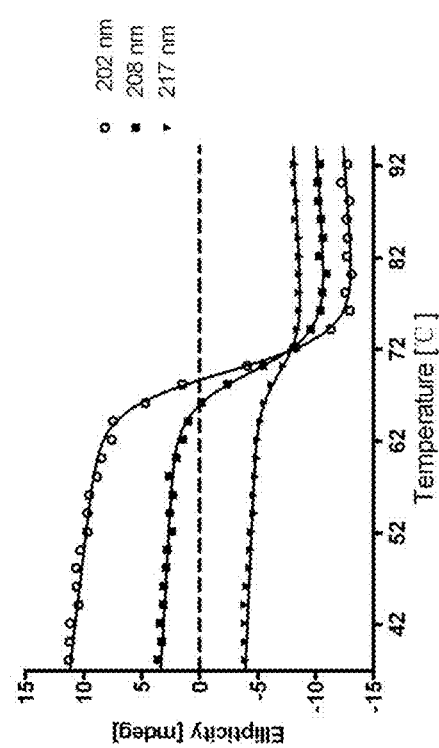
Figure 6C:
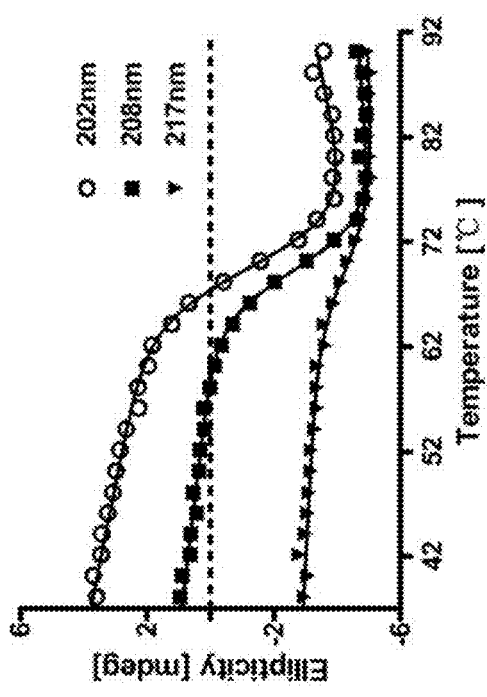
Figure 6D:
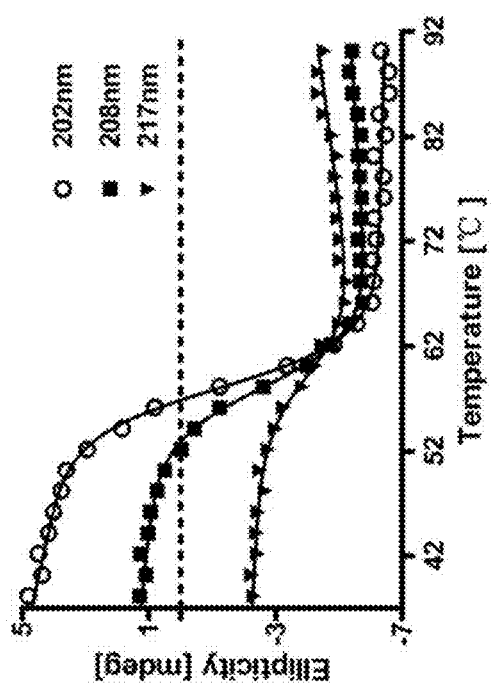
Figure 6E:
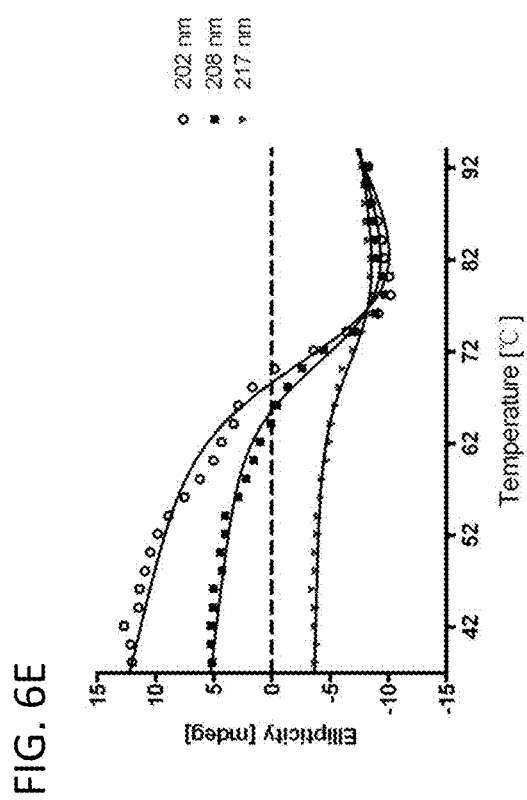
Figure 7:
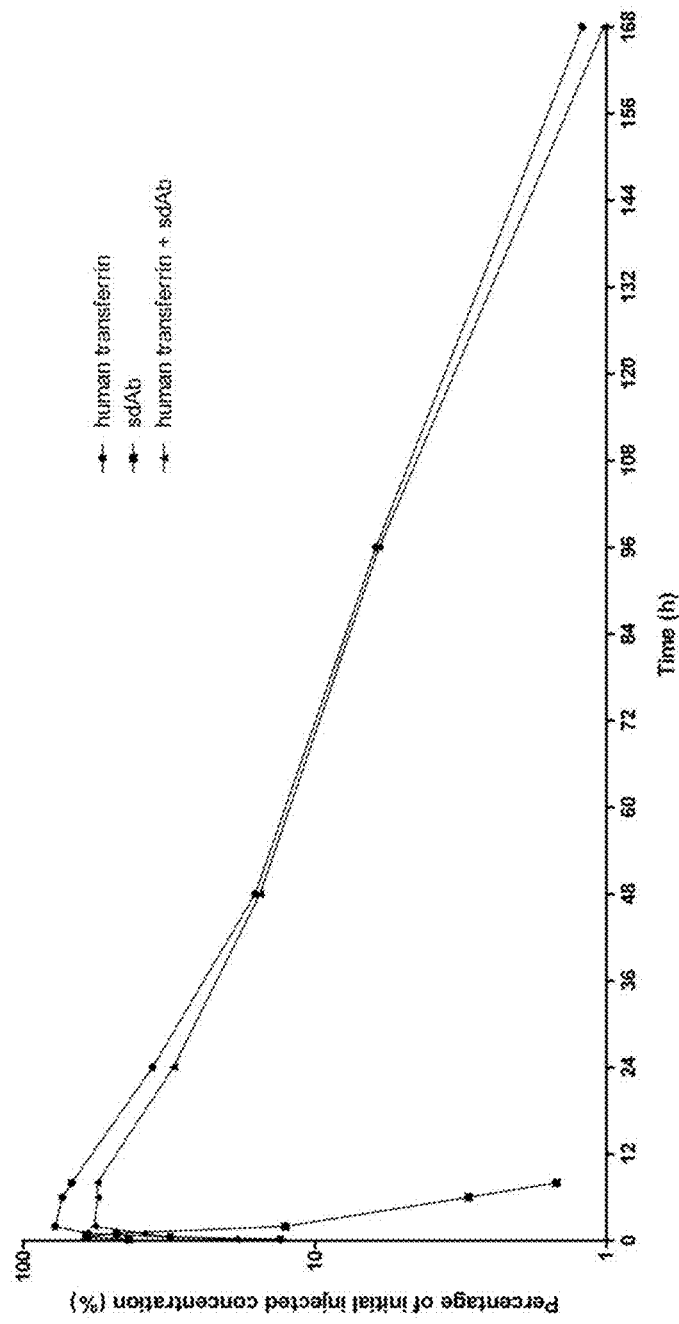
FIG. 7 shows the serum clearance of human transferrin alone, sdAb A60219 alone, and sdAb A60219 after injection into a Wister rat supplemented with human transferrin; a sample of blood was taken at the indicated timepoints and the concentrations of A60219 and human transferrin in the blood sample were determined by enzyme linked immunosorbent assay (ELISA) in three experimental groups.

CD profiles of A60219 and A60401 were measured to estimate their secondary structures and thermo half-life. Both proteins had a CD profile that is typical for single domain antibodies (Data not shown). Thermo-induced protein denaturation was measured in the temperature range from 30 to 90° C. at 2° C. intervals. Plotting the CD values at 202 nm, 208 nm, and 217 nm against temperature suggested a two phase denaturation for both A60219 (FIG. 6A) and A60401 (FIG. 6B) with a calculated melting temperature ($T_m$) of 69.8° C. and 58.7° C., respectively.

Serum Clearance of sdAb A60219

A60219 was selected to test its serum half-life based on its high affinity, pure monomeric status, and high thermo half-life. A60219 was first injected into rat either by itself or immediately after injection of human transferrin into the rats. Human transferrin was also injected to measure its serum half-life in rats, mimicking an environment of existing human transferrin in the blood. An ELISA system was employed to measure the concentrations of A60219 in rat blood taken at different time points after injection.

Blood clearance of human transferrin in Wister rats was first investigated. After injecting 30 mg human transferrin into the rats, blood samples were collected for seven days. A gradual and steady decline of transferrin concentration was observed. The $t_{1/2\beta}$ was calculated as 22 hours. This is significantly shorter than the serum half-life of human transferrin in human. Nevertheless, infusion of human transferrin in rats provides a model for us to estimate the serum half-life of A60219 in human. It is noteworthy that the anti-human transferrin antibody has no cross reactivity with rat transferrin, which makes the analysis of the serum clearance of the sdAb simple.

The serum half-life of the sdAb A60219 was then investigated. As many other sdAbs ever studied in animal models, A60219 was cleared from the rat blood rapidly. At approximately 8 hours only trace amounts of injected A60219 could be detected in the rat blood.

A60219 half-life was significantly longer in rats supplemented with human transferrin. Its blood clearance rate is very similar to that of human transferrin. The calculated serum half-life is also 22 hours. This indicates that, when injected into human, A60219 would have a similar serum half-life as human transferrin.

Results from the serum clearance study demonstrated that, exposing a polypeptide comprising an antibody or fragment thereof against a transferrin to the transferrin significantly increased the serum half-life of the polypeptide in vivo.

REFERENCES

1. Sleep, D., J. Cameron, and L. R. Evans, *Albumin as a versatile platform for drug half-life extension*. Biochim Biophys Acta.
2. Kontermann, R. E., *Strategies for extended serum half-life of protein therapeutics*. Curr Opin Biotechnol. 22(6): p. 868-76.
3. Lee, L. S., et al., *Prolonged circulating lives of single-chain Fv proteins conjugated with polyethylene glycol: a comparison of conjugation chemistries and compounds*. Bioconjug Chem, 1999. 10(6): p. 973-81.
4. Tuettenberg, J., et al., *Pharmacokinetics, pharmacodynamics, safety and tolerability of APG101, a CD95-Fc fusion protein, in healthy volunteers and two glioma patients*. Int Immunopharmacol. 13(1): p. 93-100.
5. Nolte, M. W., et al., *Improved kinetics of rIX-FP, a recombinant fusion protein linking factor IX with albumin, in cynomolgus monkeys and hemophilia B dogs*. J Thromb Haemost. 10(8): p. 1591-9.
6. Holt, L. J., et al., *Anti-serum albumin domain antibodies for extending the half-lives of short lived drugs*. Protein Eng Des Sel, 2008. 21(5): p. 283-8.
7. Walker, A., et al., *Anti-serum albumin domain antibodies in the development of highly potent, efficacious and long-acting interferon*. Protein Eng Des Sel. 23(4): p. 271-8.
8. Stork, R., D. Muller, and R. E. Kontermann, *A novel tri-functional antibody fusion protein with improved pharmacokinetic properties generated by fusing a bispecific single-chain diabody with an albumin-binding domain from streptococcal protein G*. Protein Eng Des Sel, 2007. 20(11): p. 569-76.
9. Matsubara, M., et al., *Single dose GLP-1-Tf ameliorates myocardial ischemia/reperfusion injury*. J Surg Res. 165 (1): p. 38-45.
10. Keefe, D., et al., *In vitro characterization of an acetylcholine receptor-transferrin fusion protein for the treatment of myasthenia gravis*. Autoimmunity. 43(8): p. 628-39.
11. Arbabi Ghahroudi, M., et al., *Selection and identification of single domain antibody fragments from camel heavy-chain antibodies*. FEBS Lett, 1997. 414(3): p. 521-6.
12. Tanha, J., A. Muruganandam, and D. Stanimirovic, *Phage display technology for identifying specific antigens on brain endothelial cells*. Methods Mol Med, 2003. 89: p. 435-49.
13. Zhang, J., et al., *A pentavalent single-domain antibody approach to tumor antigen discovery and the development of novel proteomics reagents*. J Mol Biol, 2004. 341(1): p. 161-9.
14. Cortez-Retamozo, V., et al., *Efficient cancer therapy with a nanobody-based conjugate*. Cancer Res, 2004. 64(8): p. 2853-7.
15. Luo, F. R., et al., *Correlation of pharmacokinetics with the antitumor activity of Cetuximab in nude mice bearing the GEO human colon carcinoma xenograft*. Cancer Chemother Pharmacol, 2005. 56(5): p. 455-64.

We claim:

1. An isolated single-domain antibody (sdAb) or antigen-binding fragment thereof that specifically binds a transferrin, wherein the sdAb or antigen-binding fragment thereof comprises a complementarity determining region 1 (CDR1), CDR2, and CDR3 having the amino acid sequences, respectively, of:
   (a) SEQ ID NO: 1, SEQ ID NO: 10, and SEQ ID NO: 18;
   (b) SEQ ID NO: 3, SEQ ID NO: 12, and SEQ ID NO: 19;
   (c) SEQ ID NO: 6, SEQ ID NO: 14, and SEQ ID NO: 21;
   (d) SEQ ID NO: 7, SEQ ID NO: 15, and SEQ ID NO: 22; or
   (e) SEQ ID NO: 9, SEQ ID NO: 17, and SEQ ID NO: 24.

2. The isolated sdAb or antigen-binding fragment thereof of claim 1, comprising the CDR1, CDR2, and CDR3 having the amino acid sequences, respectively, of SEQ ID NO: 3, SEQ ID NO: 12, and SEQ ID NO: 19.

3. The isolated sdAb or antigen-binding fragment thereof of claim 1, comprising the CDR1, CDR2, and CDR3 having the amino acid sequences, respectively, of SEQ ID NO: 6, SEQ ID NO: 14, and SEQ ID NO: 21.

4. The isolated sdAb or antigen-binding fragment thereof of claim 1, comprising the CDR1, CDR2, and CDR3 having the amino acid sequences, respectively, of SEQ ID NO: 7, SEQ ID NO: 15, and SEQ ID NO: 22.

5. The isolated sdAb antibody or antigen-binding fragment thereof of claim 1, comprising the CDR1, CDR2, and CDR3 having the amino acid sequences, respectively, of SEQ ID NO: 9, SEQ ID NO: 17, and SEQ ID NO: 24.

6. The isolated sdAb or antigen-binding fragment thereof of claim 1, comprising the amino acid sequence selected from the group consisting of:

A60219:
(SEQ ID NO: 26)
QVQLVESGGGLVQAGGSLRLSCVASGSGFGINGVIWYRQAPGKQRELVAL

IKSDGYTNYRESVKGRFTISRDDAKNTVWLQMNALEPEDTGVYYCKTPGV

PFGQGTQVTVSS;

A60401:
(SEQ ID NO: 28)
QVKLEESGGGLVQAGGSLRLSCEASGNVFTIAAMGWFRQAPGKERELVAG

ITTGGSTNYADSVKGRFTISRDNAQNTMYLQMNSLRPEDTAAYSCNAVTK

WAARVGGSAEYEYWGQGTQVTVSS;

-continued

A69449:
(SEQ ID NO: 56)
QVQLVESGGGVVQAGGSLRLSCVASGSVFSIDAMGWYRQAPGNQRELVAA

MTNAGSTNYADSVKGRFTISRDNAENTVYLQMNSLKPEDTAVYYCNARSK

LIARINNPYEYWGQGTQVTVSS;

A69433:
(SEQ ID NO: 58)
QVKLEESGGGLVQAGGSLRLSCVASGNVFGIDAVGWYRQAPGKQRELVAA

TTTSGSSTNYADSVKGRFTISRDIAKNTVYLQMDSLKPEDTAVYYCYARP

KQATLIRDDYWGQGTQVTVSS;
and

A69447:
(SEQ ID NO: 62)
QVKLEESGGGSVQAGGSLRLSCTGSGSIFPLNDMGWYRQAPGKQRELVAT

ITRGGTTNYADSVKGRFTISRDSNAKNTVYLQMNSLKVEDTAVYYCNMDN

RVGGSYWGQGTQVTVSS.

7. The isolated sdAb antibody or antigen-binding fragment thereof of claim 1, having a dissociation constant ($K_d$) of $10^{-9}$ M or less for the transferrin.

8. The isolated sdAb antibody or antigen-binding fragment thereof of claim 1, wherein the transferrin is a human transferrin or monkey transferrin.

9. The isolated sdAb antibody or antigen-binding fragment thereof of claim 1, being produced recombinantly.

10. An isolated single-domain antibody (sdAb) antibody or antigen-binding fragment thereof that specifically binds a transferrin, wherein the sdAb or antigen-binding fragment thereof comprises a complementarity determining region 1 (CDR1), CDR2, and CDR3 having the amino acid sequences, respectively, of SEQ ID NO: 1, SEQ ID NO: 10, and SEQ ID NO: 18.

11. The sdAb antibody or antigen-binding fragment thereof of claim 10, wherein the sdAb or antigen-binding fragment thereof comprises the amino acid sequence of SEQ ID NO: 26.

12. The sdAb antibody or antigen-binding fragment thereof of claim 10, having a dissociation constant ($K_d$) of $10^{-9}$ M or less for the transferrin.

13. The sdAb antibody or antigen-binding fragment thereof of claim 11, having a dissociation constant ($K_d$) of $10^{-9}$ M or less for the transferrin.

14. The sdAb antibody or antigen-binding fragment thereof of claim 10, wherein the transferrin is a human transferrin or monkey transferrin.

15. The sdAb antibody or antigen-binding fragment thereof of claim 11, wherein the transferrin is a human transferrin or monkey transferrin.

16. The sdAb antibody or antigen-binding fragment thereof of claim 10, being produced recombinantly.

17. The sdAb antibody or antigen-binding fragment thereof of claim 11, being produced recombinantly.

18. A nucleic acid comprising a cDNA or synthetic DNA encoding the isolated sdAb antibody or antigen-binding fragment thereof of claim 1.

19. An expression vector comprising the nucleic acid of claim 18.

20. A recombinant host cell comprising the expression vector of claim 19.

* * * * *